US010564067B2

(12) United States Patent
Mechrez et al.

(10) Patent No.: US 10,564,067 B2
(45) Date of Patent: Feb. 18, 2020

(54) METHODS AND APPARATUS FOR INSPECTION AND OPTIONAL REWORK OF BLOCKED OPHTHALMIC LENSES

(71) Applicant: Shamir Optical Industry Ltd., Upper Galilee (IL)

(72) Inventors: Guy Mechrez, Nesher (IL); Zohar Kadmon, Upper Galilee (IL); Ofer Markman, Upper Galilee (IS); Gil Perlberg, Zikhron Ya'akov (IL); Haim Hainebach, Upper Galilee (IL); Youval Katzman, Zikhron Ya'akov (IL)

(73) Assignee: Shamir Optical Industry Ltd., Upper Galilee (IL)

( * ) Notice: Subject to any disclaimer, the term of this patent is extended or adjusted under 35 U.S.C. 154(b) by 303 days.

(21) Appl. No.: 15/481,336

(22) Filed: Apr. 6, 2017

(65) Prior Publication Data

US 2017/0274490 A1 Sep. 28, 2017

Related U.S. Application Data

(63) Continuation of application No. PCT/IB2015/002125, filed on Oct. 7, 2015.
(Continued)

(51) Int. Cl.
*B24B 13/005* (2006.01)
*G01M 11/02* (2006.01)
(Continued)

(52) U.S. Cl.
CPC .......... *G01M 11/0278* (2013.01); *B08B 3/12* (2013.01); *B24B 9/14* (2013.01); *B24B 13/0052* (2013.01);
(Continued)

(58) Field of Classification Search
CPC .... B24B 13/005; B24B 13/0052; B29D 11/00
(Continued)

(56) References Cited

U.S. PATENT DOCUMENTS 2,838,892 A 6/1958 Blash
3,049,766 A 8/1962 Buckminster
(Continued)

FOREIGN PATENT DOCUMENTS

EP 0969956 B1 11/2004
EP 2 801 440 A1 11/2014
(Continued)

OTHER PUBLICATIONS

Partial Supplementary European Search Report dated May 15, 2018 for European Application No. 15849295.9, 14 pages.
(Continued)

*Primary Examiner* — Robert A Rose
(74) *Attorney, Agent, or Firm* — Cooley LLP

(57) ABSTRACT

An opaque adhesive can be used to secure the convex surface of a lens blank to a lens blocking piece. This opaque adhesive can include a resin that is curable under ultraviolet light and contains many dispersed pigment particles. The pigment particles may absorb light in the wavelength range of about 300 nm to about 800 nm such that the adhesive appears substantially opaque. A lens-on-block (LOB) system that uses the opaque adhesive to adhere a lens blank to a lens blocking piece facilitates on-block inspection of surface defects by increasing the contrast of light reflected from the surface being inspected. Put differently, the defects in the lens blank's surfaces stand out more when viewed in front of the opaque adhesive The inspection results can be used to carry out rework loops that eliminate or correct the detected defects, providing a streamlined method for on-block manufacturing of ophthalmic lenses.

20 Claims, 14 Drawing Sheets

Related U.S. Application Data

(60) Provisional application No. 62/060,954, filed on Oct. 7, 2014, provisional application No. 62/060,959, filed on Oct. 7, 2014, provisional application No. 62/060,966, filed on Oct. 7, 2014.

(51) Int. Cl.

| | | |
|---|---|---|
| *B29D 11/00* | (2006.01) | |
| *G01N 21/88* | (2006.01) | |
| *B08B 3/12* | (2006.01) | |
| *B24B 9/14* | (2006.01) | |
| *G01N 21/958* | (2006.01) | |

(52) U.S. Cl.
CPC .. *B29D 11/00923* (2013.01); *B29D 11/00942* (2013.01); *G01M 11/0214* (2013.01); *G01N 21/8803* (2013.01); *G01N 2021/9583* (2013.01)

(58) Field of Classification Search
USPC .................................. 451/384, 390, 42, 460
See application file for complete search history.

(56) References Cited

U.S. PATENT DOCUMENTS

| | | |
|---|---|---|
| 3,846,889 A | 11/1974 | Reisman |
| 3,962,833 A | 6/1976 | Johnson |
| 5,148,637 A | 9/1992 | Byron |
| 5,528,357 A | 6/1996 | Davis |
| 5,608,454 A | 3/1997 | Flemmer et al. |
| 5,887,326 A | 3/1999 | Bower et al. |
| 2007/0284770 A1 | 12/2007 | Ansell et al. |
| 2010/0170635 A1 | 7/2010 | Savoie |
| 2011/0033615 A1 | 2/2011 | Breme et al. |
| 2011/0070382 A1 | 3/2011 | de Rojas et al. |
| 2011/0220519 A1 | 9/2011 | Meschenmoser et al. |
| 2011/0229660 A1 | 9/2011 | Reynolds |
| 2013/0128026 A1 | 5/2013 | Hirose |
| 2014/0366363 A1 | 12/2014 | Meschenmoser et al. |
| 2016/0003986 A1 | 1/2016 | Breme et al. |
| 2017/0276568 A1 | 9/2017 | Mechrez et al. |

FOREIGN PATENT DOCUMENTS

| | | |
|---|---|---|
| JP | S61 160849 A | 7/1986 |
| WO | WO 2012/054972 A1 | 5/2012 |
| WO | WO 2013/088021 A | 6/2013 |

OTHER PUBLICATIONS

Extended European Search Report dated Oct. 8, 2018 for European Application No. 15849295.9, 16 pages.
International Search Report and Written Opinion dated Dec. 18, 2016 for International Application No. PCT/IL2016/051031, 10 pages.
"High-Speed Spindles Aid in Fabricating Plastic Eyeglass Frames with Special Finishes" Plastics Design & Processing, Dec. 1983/ Jan. 1984 p. 21.
"News For Design Engineers" Design News, Aug. 18, 1986, 3 Pgs., vol. 42, No. 16.
"Returns? Frame Devaluation", Eyecare Business, Sep. 2007, 4 Pgs.
Bargman, "OLA President's Letter" Member News, Sep. 2010, 1 Pg, Issue 7.
Bruneni, "More Than Meets The Eye, The Stories Behind the Development of Plastic Lenses," PPG Optical Materials, 1997, 40 pages.
Bruneni, "Are Lens Warranties Ready for Extinction?" Eyecare Business, Mar. 2003.
Clements, "Selection of Optical Adhesives", University of Arizona. College of Optical Sciences, Dec. 14, 2006.
Dziuban, "ANSI Z87.1-2003—The New Safety Eyewhere standard" OLA Tech Topic Member News, Jul. 2003, Issue 1.
Elma, "Elmasonic P 30 H", www.elma-ultrasonic.com, retrieved from http://www.bkinstruments.co.kr/sub2/PP_Elmasonic_P30H_EN.pdf on Apr. 7, 2017.
Granby, "The danger of no-fault warranties", Eyecare Business, Mar. 2008, 5 pages.
"How eyeglass lens is made—material, production process, manufacture, used, processing, procedure, machine, Raw Materials, Design, The Manufacturing Process of eyeglass lens, Byproducts," retrieved from http://www.madehow.com/Volume-1/Eyeglass-Lens.html on Sep. 22, 2014.
International Search Report and Written Opinon PCT/IB2015/002125, dated Mar. 6, 2016, 16 Pgs.
International Search Report and Written Opinon PCT/IB2015/002137, dated Mar. 6, 2016, 16 Pgs.
Martini, et. al., "Timing Requirements for Deposits of Employee Defferrals/Contributions and Loan Repayments" Reedsmith, Feb. 7, 2012, 1 Pgs.
Martini, et. al., "IRS Announces New Voluntary Worker Classification Program" Reedsmith, Sep. 27, 2011, 2 Pgs.
Martini, et. al., "IRS Releases Revised Health Care Reporting Guidance" Reedsmith, Jan. 11, 2012, 1 Pg.
Martinez, "Those Pesky Warranties," Vision Monday, Sep. 15, 2009, 2 Pgs., retrieved from http://www.labtalkonline.com/articles/34221 on Apr. 14, 2017.
McLean, "Operating your practice with solid AR warranty polocies helps keep both patient satisfaction and practice profitability high", Eyecare Business, Mar. 2007 , 4 Pgs.
McLean, "How low can you go?" Eyecare Business, Jul. 2005, 4 Pgs.
McLean, "Managing Warranties" Eyecare Business, Jul. 2006, 4 Pgs.
McLean, "Premake, Don't Remake", Eyecare Business, Nov. 2009, 3 Pgs.
McLean, "REDO is a four-letter word", Eyecare Business, Jun. 2006, 3 Pgs.
Morgan, "Money Happy" Eyecare Business, Sep. 2007, 1 Pg.
Torgersen, "ANSI Z87.1-2010—The Revised Standard for Protectic Eyewear" OLA Tech Topic Member News, Sep. 2010, Issue 6.
Torgersen, "Spectacle Lens Standard—Revised in 2010 ANSI Z80. 1-2010—Prescription Ophthalmic Lenses" OLA Tech Topic Member News, Jun. 2010, Issue 4.
Wilkinson, "Spectacle lens Production. From casting to freeform generation", OT, May 2006, pp. 37-42.
Yoho, "Delivering Superior Service at 100 mph", Eyecare Business. Com, Aug. 2012, 3 Pgs.
Yoho, "Free-Form Facts: An OLA-sponsored article on what goes into creating digitally surfaced free-form lenses", Eyecare Business, Sep. 2010, pp. 72,74,76.
Yoho, "Growing ECPs Through Education", Eyecare Business, Sep. 2008, 3 Pgs.
Yoho, "Labs Listen to ECPs", Eyecare Business, Nov. 2011, 3 Pgs.
Yoho, "LABS: Making Kids Eyewear Easier", Eyecare Business, Jun. 2009, 3 Pgs.
Yoho, "Lenses: The Big Picture", Eyecare Business, Mar. 2009, 3 Pgs.
Yoho, "Preventing Spoilage" Eyecare Business, Aug. 2008, 2 Pgs.
Yoho, "Processing Primer" Eyecare Business, Jun. 2010, 3 Pgs.
Yoho, "Redos and Remakes", Eyecare Business, May 2012, 3 Pgs.
Yoho, "Reducing Lab Costs", Eyecare Business, Mar. 2011, 4 Pgs.
Yoho, "Labs Give Input About Output", Eyecare Business, Mar. 2012, 3 Pgs.
Yoho, "Processing Primer", Eyecare Business, Jun. 2010, pp. 56,58, 60.
Yoho, "Exceptional Eyewear", Eyecare Business, Apr. 2008, pp. 72-78.
Yoho, "O.L.A New World" Eyecare Business, Nov. 2009, pp. 48-50.
Yoho, "Redos and the Bottom Line", Eyecare Business, Jun. 2011, 3 Pgs.
Yoho, "What's Up at OLA", Eyecare Business, Sep. 2011, pp. 70,72-74.

(56) References Cited

OTHER PUBLICATIONS

Yoho, "The Free-form Experiment", Eyecare Business, Sep. 2009, pp. 60,62,64.
Yoho, "Labs are in frame business", Eyecare Business, Nov. 2010, 3 Pgs.

METHODS AND APPARATUS FOR
INSPECTION AND OPTIONAL REWORK OF
BLOCKED OPHTHALMIC LENSES

CROSS-REFERENCE TO RELATED
APPLICATIONS

This application is a bypass continuation of International Application No. PCT/IB2015/002125, filed Oct. 7, 2015, and entitled "METHODS AND APPARATUS FOR INSPECTION AND OPTIONAL REWORK OF BLOCKED OPHTHALMIC LENSES," which claims the priority benefit, under 35 U.S.C. § 119(e), of each of the following U.S. provisional applications: Ser. No. 62/060,954, filed Oct. 7, 2014, and entitled "METHODS AND APPARATUS FOR CLEANING BLOCKED OPHTHALMIC LENSES"; Ser. No. 62/060,959, filed Oct. 7, 2014, and entitled "METHODS AND APPARATUS FOR REWORKING BLOCKED OPHTHALMIC LENSES"; and Ser. No. 62/060,966, filed Oct. 7, 2014, and entitled "METHODS AND APPARATUS FOR VISUAL INSPECTION OF BLOCKED OPHTHALMIC LENSES." Each of the prior applications identified above is hereby incorporated herein by reference in its entirety.

BACKGROUND

The advent of two technologies has enabled a streamlined method of producing complete prescription eyeglass lenses called on-block manufacturing (OBM). The first technology is a plastic and ultraviolet (UV) cured adhesive that allows lens blanks to be coupled with a lens blocking piece, also known as a block, a blocker, a lens chuck, or a surface block, that can hold lens blanks for machining. The second technology is the Full Back Side (FBS) digital surfacing technology, also referred to as free form technology or free form generation, which allows the entire prescription to be cut into the back (usually concave) surface of a lens. By convention, the back or rear surface of the lens is the surface closest to the wearer's eyes, and the front surface of the lens is the surface opposite the back surface. For a typical convex-concave lens, the front surface is convex and the back surface is concave. Other lenses may be biconcave or biconvex, with front and back surfaces that are both concave or both convex, respectively.

FIG. 1 illustrates a conventional OBM process. In this OBM process 100, based on a prescription, an appropriate lens blank with a fully processed front (usually convex) surface is first selected such that the OBM process only treats the back surface to save manufacturing time and streamline the manufacturing process. Then the lens blank is coupled to a lens block, in a step called blocking, by gluing the front surface of the lens blank to the lens block using a UV-curable adhesive. The lens block holds the lens blank while the concave surface of the lens blank is machined to fill the prescription. To further reduce manufacturing time, lens blanks can be pre-blocked, i.e., the lens blank can be affixed, bonded, glued, or otherwise secured to the lens block before arriving at the OBM facility.

After the lens blank has been blocked (also referred to as lens on block), its back surface is machined in two phases: a coarse machining phase at step 110 to generate the overall shape (e.g., using a generator), and a fine machining phase at step 130 to polish the surface and achieve the desired surface qualities. An engraving step 120 can be performed between the coarse machining and the fining machining to engrave semi-visible and/or visible marks on the lens to, for example, guide subsequent manufacturing steps. After the back surface machining, the back surface is usually cleaned at step 140 and dried at step 150 before being coated with, for example, a hard coating at step 160 and/or an anti-reflection coating at step 170. Then the coated lens is removed, in a step 180 called deblocking, from the lens block for edging, which involves cutting the lens into an appropriate shape to fit the lens frame. An off-block inspection step 190 can be performed after the lens is removed from the block.

The OBM process can normally produce a pair of eyeglass lenses in less than a business day or two. Depending on the business model, some OBM labs offer a guaranteed delivery time of less than 8 hours, less than 3 hours, or less than 90 minutes. The guaranteed delivery time can be measured from receiving a prescription to a point at which the framed eyeglasses are ready for shipment. In some fast OBM labs, for example in urban areas, the guaranteed delivery time can include the shipment as well.

Unfortunately, defects near (on or beneath) the back surface of the lens blank may render the finished lens unsuitable for filling the prescription, i.e. the lens parameters are out of a specified range of tolerance. These defects include but are not limited to scratches, dirt, cracks, smudges, or pieces of lint on the lens surface. Defects may be introduced during the machining process or from exposure to the surrounding environment during the OBM process. A hairline scratch on the lens surface introduced during the fine machining phase, for example, can cause a defective anti-reflection coating, reducing the manufacturing yield.

To increase manufacturing yield, a lens may be inspected for defects before coating. However, during conventional inspection, an inspector looks through the lens to identify any defect. Accordingly, the lens is usually deblocked before inspection in order to transmit light through the front and back surfaces, and reblocked again after inspection for subsequent processing steps (e.g., coating). Deblocking and reblocking consumes extra time and can disrupt the OBM process.

SUMMARY

Exemplary embodiments of the present invention include methods and systems of processing a blocked lens while the lens blank stays affixed on the lens blocking piece so as to avoid disrupting the otherwise streamlined manufacturing process and improve the manufacturing yield. On-block processing includes inspection and reworking.

In one exemplary embodiment, an opaque adhesive is employed to couple a semi-finished lens blank to a lens blocking piece to facilitate on-block inspection. The opaque adhesive comprises a curable resin, and pigment particles that are dispersed into the resin via high shear mixing to generate the desired opacity. In one example, the pigment particles are solid, such as carbon black. In another example, the pigment particles are dissolved in liquid, including aniline, or chromophoric dye.

In another exemplary embodiment, a method of inspecting a blocked lens is provided, wherein the blocked lens includes a lens blank affixed to a lens blocking piece, and an opaque material in optical communication with the front and back surfaces of the lens blank. In the method, the opaque material is illuminated by a visible light via the back surface of the lens blank, so as to render at least one defect near the back surface of the lens blank visible to a human eye. The defect includes optical defect, coating defect, cosmetic defect, or their combinations.

In yet another exemplary embodiment, a method of reworking a blocked lens is provided. In the method, following processing the back surface of a blocked lens, an on-block inspection is performed to examine the quality of the back surface. In response to detection of one or more correctable defects, the blocked lens is then reworked. The reworking steps include machining, polishing, coating, tinting, or cleaning the back surface of the lens blank to cure the detected defect.

On-block inspection and subsequent reworking steps can be performed at one or more of the following points in a lens manufacturing process. In one example, the inspection is carried out before hard coating. Detected defects, including scratch, crack, dig or dent, are remedied by machining and polishing the back surface of the lens blank. In another example, the inspection is performed after the hard coating to check the coating quality. Defects on the coating are corrected by altering the shape of the back surface, on which a second coating is then deposited. In yet another example, the method further comprises a second inspection to examine the lens quality after reworking steps. In yet another example, the method further comprises an on-block inspection after the cleaning step to examine the blocked lens after cleaning. Upon the detection of curable defects, reworking steps are carried out for correction. In yet another example, multiple inspection and rework cycles are performed at different points in a single lens manufacturing process.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The skilled artisan will understand that the drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

DETAILED DESCRIPTION

Figure 1:
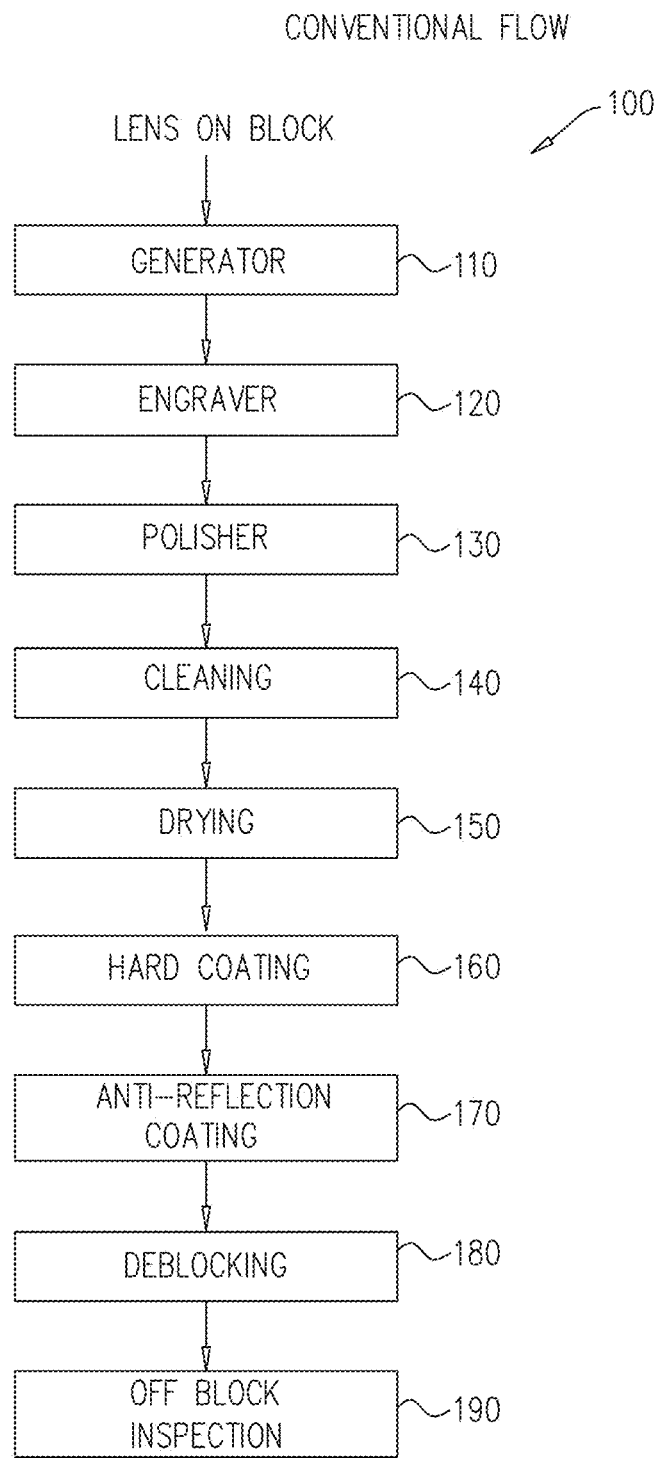
FIG. 1 is a flowchart that illustrates a conventional on-block manufacturing (OBM) process.

Before detailed description of exemplary embodiments, clarification of terms and parameters used in this application may be helpful in understanding aspects of the disclosed technology. Unless otherwise stated, in this specification:

1) The concave surface of the lens blank can also be referred to as the back surface;
2) The convex surface of the lens blank can also be referred to as the front surface;
3) "Near a surface" means on, below, and/or within the surface; for lenses coated with one or more layers, "near" means on, below, and/or within the coating layer(s);
4) A coating system: Multi-layered structure comprising coating layers of various thicknesses and material properties (see, e.g., FIG. 3, TABLES 1 and 2);
5) Coating system on front side: coating application performed prior to blocking (connecting lens to block);
6) Blocked lens, lens block assembly, and Lens on Block (LOB) refer to the assembly of a lens blank coupled to a lens block, including any adhesive layers, coating systems on the front and/or rear surfaces of the lens blank, and coatings on the lens block;

7) Damage to a coating layer can include, but is not limited to: scratch, cracking, abrasion, delaminating, and changes in a coating layer's mechanical, structural, thermal or optical properties;
8) Damage to a coating system can include, but is not limited to: delamination between coating layers, solvents (e.g., aqueous solutions and organic solutions) between coating layers, swelling of solvents into the matrixes of the coating layers, cosmetic defects (e.g., curing defects), changes to the physical interactions among coating layers, changes in mechanical, structural, thermal, or optical properties of the system, and undesired adhesion between upper most layer of the coating system on convex side and the lens block or other surface;
9) Surface contaminants can include, but are not limited to: residue from the machining and/or polishing processes, aluminum oxide, airborne particles, and residual particles from the milling processes, swarf (i.e., fine chips or filings of stone, metal, or other material produced by a machining operation), biofouling, oil-based contamination, organic contamination from handling and/or from material machining processes, mineral deposits based scale, particles and precipitations;
10) Damage to the UV-curable adhesive layer can include, but is not limited to changes in viscosity, glass transition temperature, transparency to visible light, color, tensile strength, Young's modulus, elongation at failure, yield stress, and other optical, thermal, and mechanical properties;
11) Properties of the adhesive layer after UV curing (between upper most layer of the coating system on convex side and the block) include, but are not limited to, tensile strength, Young's modulus, torque strength, peel strength, cross linking density, and heat capacity;
12) A prescription of a lens can include parameters that specify the desired properties of the lens and the processes of manufacturing the lens. For example, a prescription can be the output of a prescriptor, which converts a medical prescription provided by an eye care professional (ECP) into a detailed instruction of lens manufacturing, including optical power, surface shape, surface roughness, dimensions, material, coating type, color, and machines to be used and their operating parameters, among others;
13) A rework step can mean a repeat of any of the procedures in lens manufacturing, including generating, polishing, cleaning, and coating, among others. A rework step can be performed to correct a defect, to improve lens quality, or to prepare the lens for subsequent processing (e.g., cleaning rework);
14) A rework loop can include one or more manufacturing steps and their repeats to achieve a desired property. For example, a cleaning rework loop can include cleaning-inspection-cleaning cycles until the surface cleanliness satisfies certain standard; and
15) An opaque layer or material or substance refers to a layer that does not transmit light in a particular spectral region, e.g. the visible region between 300 nm and 800 nm.

On-Block Manufacturing with On-Block Inspection and Reworking

The on-block manufacturing (OBM) process is a less aggressive manufacturing process compared to conventional procedures. Unlike conventional ophthalmic lens manufacturing processes, OBM of the concave surface produces negligible residual forces and/or strains on the opposing convex surface. Thus, with the OBM process, the lens's optical properties can be measured on the block, provided that the blocked lens has the desired opacity or reflectivity to support such a measurement. If the measurement results show a problem with the optical properties of the machined lens, the problem may be corrected with another processing step, called "reworking." Reworking can include cleaning, machining, polishing, tinting, coating, and/or their combinations.

Figure 2:
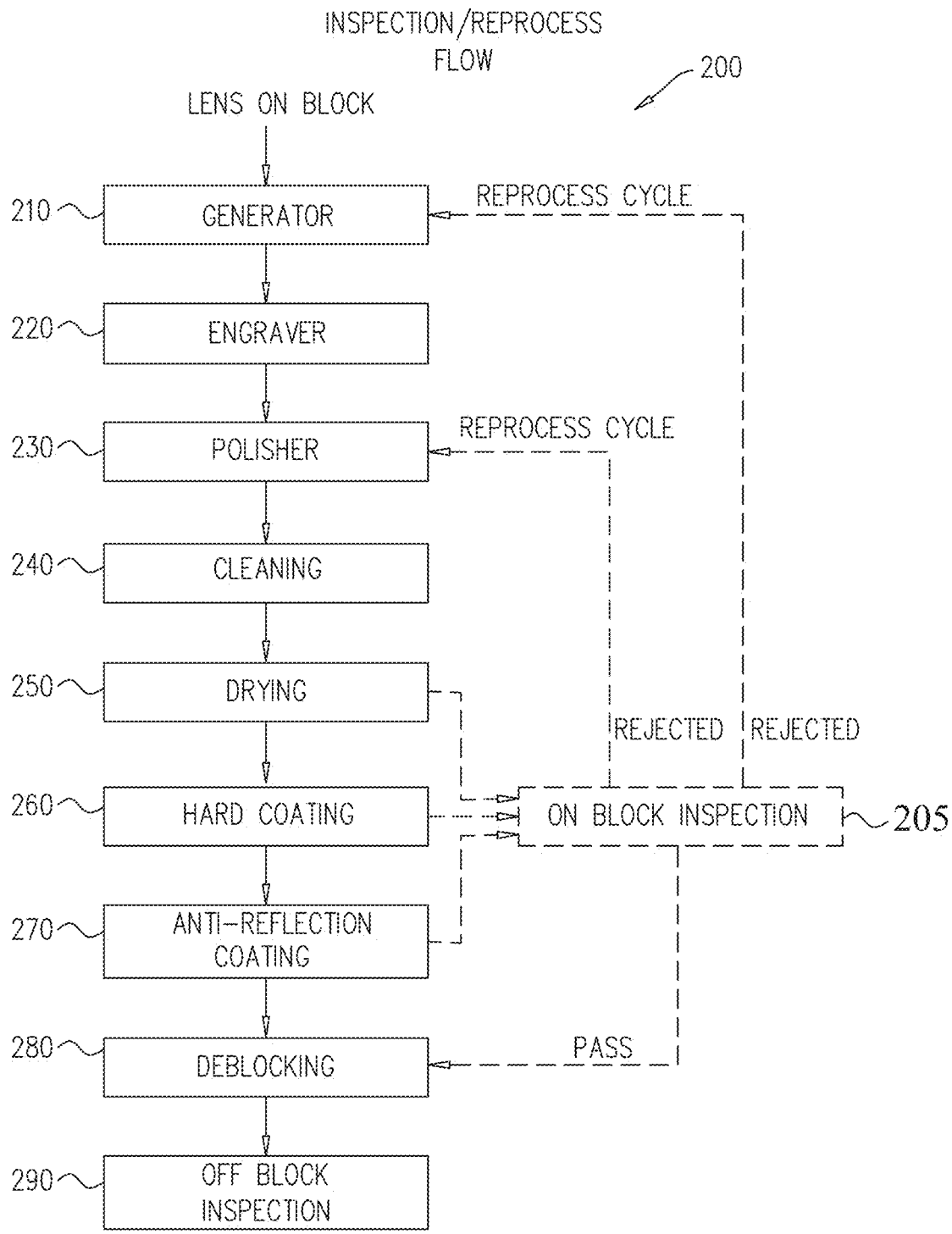
FIG. 2 is a flowchart that illustrates an OBM process including on-block visual inspection and reworking of a blocked lens blank.

FIG. 2 is a flow chart that illustrates an on-block manufacturing (OBM) process for ophthalmic lenses that includes on-block inspection, reworking, and cleaning of lens blanks. The OBM process 200 includes on-block inspection 205 at (or after) one or more stages during lens manufacturing, rework loops in response to the inspection 205 (if applicable), and on-block cleaning after machining and/or in response to detection of certain defects in the inspection step 205. The inspection step 205 and applicable rework loops can be carried out, for example, after cleaning (e.g., step 240) to examine whether there is any defect introduced by machining (provided that the cleaning has removed all debris that might interfere with the inspection) and to provide a good surface for hard coating. The inspection 205 can also be performed after coating steps to verify the coating quality. Furthermore, the lens optical properties can be measured or evaluated on-block.

With on-block inspection capability, a modified on-block manufacturing (OBM) 200 of eyeglass lenses can include the following steps:
1) Receiving a semi-finished lens blank with a coated front surface (usually a convex surface);
2) Blocking the lens blank (to form a lens on block, or LOB) by gluing the front surface of the lens blank to a blocking piece with an opaque black adhesive or sealing to allow on-block inspection and measurements;
3) Machining (e.g., milling and/or turning) the uncoated back surface of the lens blank with a free form generator supported by appropriate software to facilitate automated machining at step 210;
4) Engraving semi-visible marks on the back surface of the lens blank at step 220;
5) Polishing the back surface of the lens blank at step 230, e.g., with a polisher that is separate from the generator or housed in the same machine as the generation equipment;
6) Cleaning the concave surface of the lens blank at step 240 (e.g., via ultrasonic cleaning, high pressure steam cleaning, or any other suitable type of cleaning method);
7) Drying the cleaned lens block at step 250 (e.g., via cold/hot air flow, heating, etc.);
8) Optional on-block inspection 205 and reworking of the lens blank's back surface;
9) Applying a hard coating layer to the lens blank's back surface at step 260;
10) Optional on-block inspection 205 and reworking of the back and/or front surfaces of the lens blank;
11) Applying an anti-reflection coating layer to the back surface of the lens blank at step 270;
12) Optional on-block inspection 205 and reworking of the lens blank's back and/or front surfaces;
13) De-blocking the lens blank from the lens blocking piece at step 280;
14) Off-block inspection of the lens blank at step 290;
15) Marking the lens orientations with visible markings for alignment in the edging process; and 16) Edging the lens blank to form the lens shape for the selected frame.

The sequence or order of the above steps may be altered or adjusted in different specific situations. For example, edging and marking can precede de-blocking 280. Moreover, engraving 220 can be performed after polishing 230 and can be applied on the front surface before blocking.

In addition, in the above process, the optional on-block inspections 205 can allow several possible rework loops to increase the manufacturing yield of the process. Generally, the inspection 205 may result in at least three types of outcomes. In one scenario, when the inspection results are within a predetermined range of specification thresholds, no reworking is needed and the lens block is ready for next step. In a second scenario, when the inspection reveals a minor defect, such as contamination, or a minor scratch, the lens can be sent for cleaning 240, or polishing 230 that can remove the contaminant or scratch but may not significantly alter the optical power, i.e., the possible change of optical power is within the tolerance range specified in the prescription (e.g., less than 0.125 Diopter). In a third scenario, the inspection may reveal that the lens has major defect, such as an out-of-specification coating, incorrect optical power, a deep scratch or dent, in which case a repeat generation (e.g., via step 210) may be performed to cure the defect. The repeat generation may involve machining the lens according to a modified prescription which accommodates the rework loops by specifying a slightly different lens parameter, such as lens thickness.

On-block inspection 205 may examine, or measure, or evaluate one or more of the following properties of the lens blank: optical power, lens curvature, lens center thickness, lens edge thickness, lens weight, surface reflectivity, mechanical strength, surface roughness, optical transmission, color, or cleanliness of the manufactured lens. In response to deficiency of each property, a corresponding rework procedure (machining, polishing, coating, tinting, or cleaning the back surface of the lens blank) can be performed for correction. Below is a description of several non-limiting examples to illustrate possible rework loops.

In one example, an optional on-block inspection 205 can be performed after cleaning 240 or drying 250 to ensure that all contaminants have been removed during the cleaning 240. If not, the blocked lens can be cleaned again, e.g., by repeating the cleaning 240 and drying 250 process, by immediately wiping the lens at contaminated locations with a solvent like ethanol or acetone, etc. This inspection 205 can also detect possible optical defects such as scratches on the back surface, in which case the rework can be performed by a free form generator, which can have both coarse machining (e.g., as in step 210) and fine polishing (e.g., as in step 230) capabilities.

In another example, on-block inspection 205 can also be performed after the hard coating step 260 and/or the anti-reflection coating step 270. If defects are detected, the back side of the lens can be machined (e.g., via a repeat step 210) or polished (e.g., via a repeat step 230), by an amount from about 1 micron to about 100 microns (e.g., from about 5 microns to about 50 microns) to remove the coating layers but not necessarily the lens materials. This may remove the defect while substantially preserving the optical power (prescription) of the lens.

In yet another rework example, the lens power, or other optical properties, can be measured and mapped at step 205 after cleaning 240 or drying 250, after coating (hard coating 260 and/or anti-reflection coating 270), but prior to de-blocking 280 and/or prior to edging. For example, the optical properties of the lens can be measured on the block after coating (hard coating 260 and/or anti-reflection coating 270). The optical properties of the lens can also be measured on the block before or after edging. If the measured power is out of a preset specification threshold range, the lens-on-block can be reworked, for example, by milling the back side of the lens to achieve the desired prescription.

The rework step can comprise machining, milling, polishing, grinding, turning, engraving, or cutting the back surface to remedy possible defects. For example, if the defect is a scratch or a dig that is deeper than 0.5 micron, the back surface of the lens blank can be milled instead of or in addition to being polished. The milling, polishing or other machining process can remove a layer of substantially constant thickness, and the material removal can be substantially perpendicular to the back surface to preserve the optical properties of the lens, i.e. the material removal is conformal to the surface shape of the lens.

Repeat generation may be employed to correct possible defects, followed by a repeat polishing process, which can be brief (e.g., about 5 seconds). The overall repeat process, including configuration of the required tools, may take 1-30 minutes. In these repeat generation or polishing processes, a modified prescription may be provided to accommodate the reworking by specifying, for example, new thickness the lens.

Rework steps may be repeated more than once to form rework loops that can ensure the lens quality and improve manufacturing yield. Rework loops can be either local or global. Local rework loops, in operation, aim at satisfying one parameter or a subset of parameters in the prescription or specification. Global rework loops, on the other hand, can incorporate more than one local rework loops to form a substantially complete lens manufacturing process, e.g., from receiving an order to the completion of the coating steps. One objective of global loops can be cooperation and coordination of local rework loops so as to produce a lens that satisfies all parameters in the specification.

Exemplary local rework loops may include cleaning loops, coating loops, machining loops, or tinting loops, among others. In the cleaning loop, the desired degree of contaminant removal can be achieved by repeating the cleaning-inspection-cleaning cycles. Coating loops can include repeating coating-inspection-machining-cleaning-coating cycles until the coating quality (e.g., low reflection, uniformity, surface hardness, etc.) is within a prescribed range. Machining loops may be formed by machining-cleaning-inspection-machining cycles to fulfill a desired optical power. Notice that there can be one rework loop inside another. For example, a machining loop can include a cleaning loop, which can ensure surface cleanliness, or make sure that, for example, a certain detected defect is not a contaminant but a surface scratch.

Global loops can combine more than one of the local loops and can be a complete manufacturing process, for example, as the one shown in FIG. 2. Since the quality of the lens after most stages in the global loop is examined and verified, lenses manufactured using this process loop 200 have higher chances of meeting quality assurance requirements.

It is worth mentioning that in current industry practices, most lens blanks have a convex front surface and a concave back (rear) surface. However, in some cases, the lens blank may have a bi-convex or bi-concave configuration, in which both surfaces are convex, or concave, respectively. Alternatively, the lens blank may have a concave front surface and a convex back surface. Conventionally, back surface of a lens blank refers to the surface closer to human eyes under normal wearing conditions of eyeglasses, and front surface refers to the surface opposite the back surface. Methods and apparatus described in this application apply to all configurations of lens surfaces, although some modifications (e.g., altering the surface of the lens blocking piece to receive lens blank) may be helpful.

On-Block Visual Inspection and UV-Curable Black Adhesive

To facilitate on-block inspection, an opaque adhesive can be applied between the front surface of the lens blank and the lens block such that any defect on or near the back surface of the lens blank can be visually detected by monitoring light reflected by the back surface. If defects such as dirt, lint or stains, are detected, on-block cleaning steps can be carried out. If, however, the defects comprise scratches or other types of surface roughness, an appropriate rework loop may be performed to provide the desired surface quality. The black adhesive can also be compatible with the on-block cleaning steps, in which an ultra-sonic wave or a high pressure steam can be used. On-block cleaning does not significantly degrade the black adhesive's adhesion properties, nor does it stain or contaminate any other component of the lens block assembly that includes, among others, the lens blank, front-surface coating system, and the lens blocking piece.

A lens blank can be affixed to the lens blocking piece with a radiation-curable adhesive (also referred to as radiation-curable coatings or radiation curing coatings), which is cured by irradiating the coating with light within a specific range wavelengths (e.g., the ultraviolet (UV) range between about 100 nm and about 400 nm). In comparison with other adhesives, radiation-cured adhesives (e.g., UV-curable resins) can emit fewer volatile organic compounds (VOCs), consume less energy, and have a shorter curing time. UV-curing is also useful for affixing a transparent component to another component. More specifically, the UV-curable resin can be disposed on an interface between the transparent component and the other component (e.g., between the lens blank and the lens blocking piece), then the UV-curable resin is irradiated with UV light transmitted through the transparent component. This curing process is sometimes referred to as "through-curing."

In order to adapt radiation-curable adhesives for lens blocking and on-block inspection, black or other opaque pigments can be added into the adhesive materials to create an opaque background for defect detection while the lens blank remains blocked. However, doping radiation curable adhesives with pigments may interfere with the curing process and subsequent adhesion. Without being bound by any particular theory or mode of operation, the adhesive forces may be lower because of competition between the introduced pigments and the photoinitiators in the adhesive materials (e.g., resin) for light absorption during through-curing. More specifically, the pigments can absorb the light that would otherwise stimulate curing via absorption by the photoinitiators. Furthermore, the pigment particles may also scatter away the incident radiation, thereby diminishing the absorption and thus curing of the adhesive materials.

These concerns can be addressed, at least in part, by reactive oligomer/monomer combinations with high acrylate functionality, a suitable and effective blend of long- and short-wave absorbing photoinitiators, and a careful selection of pigment type and pigment concentration. Moreover, the combination of black pigments with certain additives can also be helpful to achieve both satisfactory opacity for lens defect inspection and through-curing for securing the lens blank to the lens block. The degree of opacity can be characterized by several parameters, such as mass attenuation/absorption coefficient, optical (penetration) depth, or any other parameters known in the art.

The resulting opaque adhesive, according to one exemplary embodiment, comprises a base adhesive (e.g., resin) and an additive (e.g., a pigment), to make the resulting adhesive black or substantially opaque. Nucleo adhesive UV 307A Eimer (Satisloh GmbH), and other silicon based (e.g., Polysiloxane) or acrylic and epoxy based adhesives can be used as the resin. The pigment, for example, can be a UV transparent black pigment including, but not limited to, carbon black, charcoal, aniline, and their combinations. Note that the pigment can be either liquid or solid. The liquid pigment can be miscible in the polymer matrix of the resin.

The incorporation of the pigments within the resins can be carried out by a purely physical process, i.e., no chemical reaction between the pigments and the resin is necessary. For example, high shear mixing (e.g., using an UltraTurraxe® high-performance dispersing instrument produced by IKA® WORKS, Inc.) can be employed to achieve the dispersion of pigments in the resin. Without being bound any particular theory or mode of operation, fluid usually undergoes shear when one area of fluid travels with a different velocity relative to an adjacent area. A high shear mixing process can be performed by a high shear mixer, which can comprise a rotating impeller or high-speed rotor, or a series of such impellers or inline rotors, powered by an electric motor. The tip velocity, or the speed of the fluid at the outside diameter of the rotor or impeller, is usually higher than the velocity at the center of the rotor or impeller, therefore creating shear and dispersing one phase or ingredient (liquid, solid, or gas; also referred to as the minor phase) into a main continuous phase (liquid; also referred to as the major phase), and resulting in exfoliation of the minor (additive or filler) phase within the major phase.

In addition to shear creation and thus pigment dispersing, the high shear mixer can also exfoliate the pigment particles. Fine exfoliation allows for the formation of a uniform black color of the resin, thus facilitating inspection of the lens for defects in an OBM process. The pigment exfoliation procedure can be carried out at a constant temperature of, for example, 25° C.

To facilitate pigment dispersing and particle exfoliation, one or more of the following design factors of the high shear mixer can be tuned: the diameter of the rotor and its rotational speed, the distance between the rotor and the stator, the time of mixing, the number of generators in the series, the number of rows of teeth, their angle, and the width of the openings between teeth.

In addition to the design and operation parameters of the high shear mixer, several other parameters may also influence the opacity or blackness of the resulting black adhesive. A first parameter is the concentration of pigments in the resin. Higher concentration increases the opacity, but may also decrease the adhesive strength. A practical range of pigment concentration can be from about 0.01% by weight (wt %) to about 15 wt %, or from about 0.1 wt % to about 1 wt %. Furthermore, particle size can also have effect on the opacity and can be adjusted by the high shear mixing process through the exfoliation effect, described above.

In addition to the opaque adhesive described above, which is UV curable, as an exemplary and non-limiting curing method, other adhesives and curing methods can be utilized to obtain suitable adhesion. These curing methods can include, but are not limited to, radiation curing (using wavelengths outside the UV range), heat curing, moisture curing, condensation curing, chemical curing, anaerobic curing, and pressure curing, among others.

The resulting black adhesive can be characterized by its thermal, rheological, and mechanical properties. Furthermore, these properties can be compared with those of the non-modified adhesive (the resin). The comparison can indicate that the UV curing (also referred to as hardening) process does not significantly change the adhesive properties of the resin.

In one example, the black adhesive can be characterized by a parallel plate rheometer. The viscosity can be measured during UV curing process. The viscosity of the resin before curing can range from about 100 centipoise (CP) to about 10000 CP. After the curing process the viscosity can undergo a significant increase reaching a viscosity range of about 100,000 CP to about 10 million CP.

Other characterization methods include, but are not limited to: 1) Differential Scanning calorimetry (DSC), which can perform thermal analysis to find out the degree of curing of the black adhesive; and 2) Dynamic Mechanical Thermal Analysis (DMTA), which can record the temperature-dependent visco-elastic properties and determines the modulus of elasticity and the damping values by applying an oscillating force to the resulting black adhesive.

After the fabrication of the lens block assembly (a lens blank coupled to a lens block) based on the modified adhesive, the system can be tested, for example, in the lens blocking facility to verify the adhesive strength and lens orientation. A tensile test, in which the lens blank is pulled away from the lens blocking piece, can also be carried out to determine that the adhesive properties of the modified adhesive are suitable for the manufacturing process.

In some examples, on-block inspection can be performed using a black coating layer. The black coating may be created by exposing the blocked lens blank to a solution, also referred to as an ink. The ink can contain micrometer-scale carbon black powders that can migrate into and become lodged in micro-scale defects that are located on the surface of the lens. In this scenario, the microscale defects can be accentuated as black, and therefore can be observed upon visual inspection. After defect detection or defect correction, if necessary, the ink can be removed to restore the transparency of the blocked lens. This can be done, for example, by rinsing with water or other solutions.

The carbon black solution can be prepared according to one or more of the following steps. First, a surfactant aqueous solution is prepared by adding a surfactant Sodium Dodecyl Sulfate (SDS) into de-ionized (DI) water, followed by magnetic stirring at a temperature of about 60° C. Micron-scale carbon black powder can then be added to the surfactant aqueous solution at a concentration range of about 0.01 wt % to about 20 wt %. A subsequent ultra-sonication step at a temperature of 0° C. can further disperse the carbon black powder in the solution, improving the uniformity of powder distribution.

Lens Blocking

Figure 3:
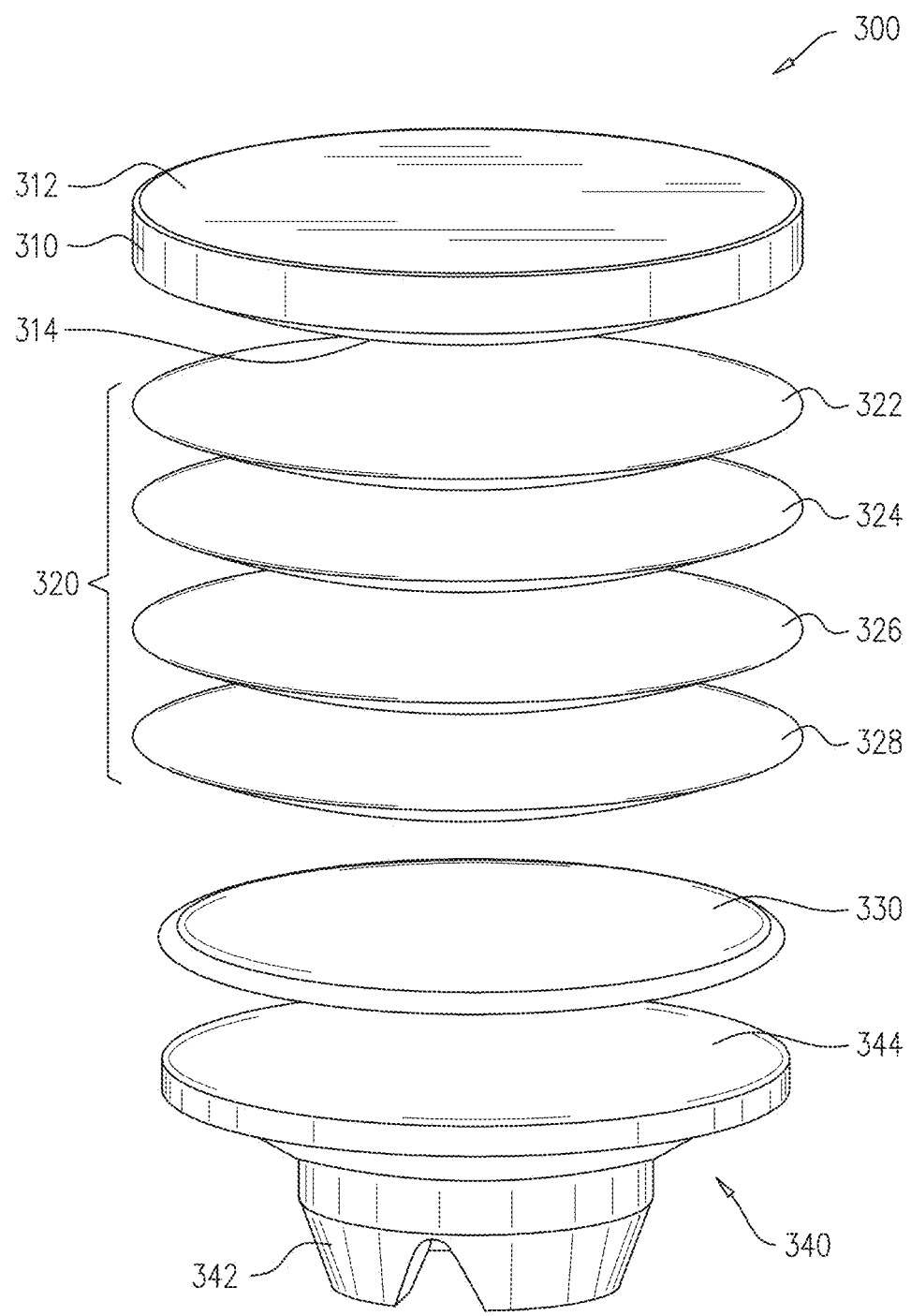
FIG. 3 is an exploded view of a blocked lens, including a lens blank with a back surface and a front surface, layers of hard coating, anti-reflection coating, top coating and grip coating on the back surface of the lens blank, a lens blocking piece, and an opaque adhesive layer that affixes the lens blocking piece to the front surface of the lens blank.

FIG. 3 shows an exploded view of a blocked lens 300 that can be used in OBM processing according to the process illustrated in FIG. 2. The blocked lens 300 includes a lens blank 310 with a back surface 312 and a front surface 314. The front surface 314 may be coated with multiple layers, collectively referred to as coating layers 320. The coating layers 320 can include, for example, a hard coating 322, an anti-reflection coating 324, a hydrophobic top coating 326, and a grip coating 328, among others. Additional coatings may include an anti-fog coating, a mirror coating, or a polarization coating, which are not shown in FIG. 2.

The front surface 314 of the lens blank 310 is affixed to a lens blocking piece 340 with a layer of adhesive 330, such as an opaque resin like those described above. More specifically, the adhesive 330 is disposed in contact with both the front surface 314 (or, more precisely, with the top most coating layer, e.g., the grip coating 328 on the front surface 314) and a receiving surface 344 defined by the lens blocking piece 340. The adhesive 330 can be cured with UV light transmitted through the lens blank 310 or the lens blocking piece 340, which also defines an exposed surface 342.

The lens blank normally has a diameter of about 50 millimeters to about 100 millimeters depending on, for example, lens frame shape and size, inter-pupil distance, frame bridge size, or frame effective diameter, among others. A range more frequently used can be from about 65 millimeters to about 85 millimeters, within which 75 mm can be a frequently used value in industry practices. The corresponding lens blocking piece 340 can substantially embrace the lens blank 310 to provide firm support during lens machining or other processing steps. In one example, the diameter of the lens blocking piece 340 can be slightly larger than that of the lens blank 310 so as to more securely hold the lens blank 310. In another example, however, the diameter of the lens blocking piece 340 can be slightly smaller than that of the lens blank 310 (e.g., to leave an overhang of about a few millimeters) to facilitate the deblocking processes if needed.

The Lens blank 310 can be made of various materials, including glass, plastic, polycarbonate, resin, NXT polymers (e.g., Trivex® material), or any other material known in the art. The material for the lens blocking piece 340 may depend on the curing method for the adhesive layer 330. For example, if UV adhesive curing is required, it can be helpful to select a material transparent to UV light (e.g. thermoplastic) for the lens blocking piece 340, such that the blocking piece 340 can transmit the UV light through to the adhesive layer 330.

The assembly (also referred to as lens on block, or simply LOB) of a lens blank 310 coupled with a lens block 340 can be coated with multiple layers as shown in FIG. 3. Non-limiting example layers may comprise: an adhesive layer, silica grip layer, satin hydrophobic layer, etc., as listed in Table 1 and Table 2. Table 1 provides an overview of the coating layers that may be used in OBM processes, while Table 2 is a detailed non-limiting example.

TABLE 1

| Lens and coating complex | | |
| --- | --- | --- |
| Layer/Material | Physical Thickness | FIG. 3 |
| Lens blocking piece | | 340 |
| Adhesive | 0.5-3 mm | 330 |
| Black spray paint | 1-100 um | Not shown in FIG. 3 |
| Grip coat | 1-20 nm | 328 |
| Hydrophobic layer | 1-20 nm | 326 |
| AR coating | 0.1-1 um | 324 |
| Hard coating (HC) | 1-10 um | 322 |
| Lens | | 310 |

TABLE 2

One example of lens and coating structures used in OBM processes

| Layer/Material | Physical Thickness (nm) | Refractive Index | Layer No. |
|---|---|---|---|
| Block piece | | | |
| Adhesive | | | |
| Black spray paint | | | |
| Silica (grip layer) | 15 | 1.39 | 9 |
| Satin (Super hydrophobic layer) | 10 | 1.21 | 8 |
| Silica | 96 | 1.46 | 7 |
| Indium Tin Oxide (ITO) | 4 | 2.06 | 6 |
| Zirconia | 56 | 1.97 | 5 |
| Silica | 27 | 1.46 | 4 |
| Zirconia | 31 | 1.97 | 3 |
| Silica | 144 | 1.46 | 2 |
| Chromium | 0.6 | 2.20 | 1 |
| Hard coating (HC) | 3000 | 1.6 | |

According to one exemplary embodiment, a lens production process can be performed when a lens blank 310 is mounted on a lens block piece 340 with the front surface 314 of the lens blank 310 secured to the lens block piece 340. In some cases, the processing of the convex surface 314 can be completed, e.g., including coating, during the preparation of the lens blank 310. Accordingly, the manufacturing can be performed substantially on the rear surface 312 of the lens blank 310. The coupling between the front surface 314 and the lens block 340 can be achieved by using a black adhesive 330 described in the previous section. Alternatively, a thermoset adhesive, which can be moisture cured, may also be employed to glue together the lens blank and the lens block. Other types of adhesive with different curing methods such as condensation curing, heat curing, chemical curing, anaerobic curing or pressure curing can also be used.

The lens block piece 340 can be used in an automated manufacturing process by including a clamping portion that can be coupled to a machine or apparatus for lens processing. Mineral glass or plastic materials can be used to make the lens block piece 340. In one example, the lens block piece 340 is disposable, i.e., the lens block piece 340 is used only once. In another example, the lens block piece 340 can be reused after lens deblocking and appropriate cleaning of the block surface that receives the lens blank.

On-Block Lens Inspection

After the machined lens blank has been cleaned (e.g., using ultrasonic cleaning, high pressure steam cleaning, or any other suitable cleaning method), the blocked lens can be inspected. The inspection can be performed on the back surface of the lens blank, in the bulk of the lens blank, on the front surface of the lens blank, and/or on the coating layers over the front surface. In operation, the on-block inspection can identify defects in regions above the adhesive layer, which can be opaque.

In conventional industry practices, when a lens is mounted on a blocking piece, the front surface is fastened to the block piece with an adhesive. The adhesive may be composed of multiple layers comprising multiple materials. Usually, neither the adhesive nor the block pieces (conventionally made of metal) are sufficiently transparent to enable visual inspection through the conventionally blocked lens. As a result, the lens blank is deblocked (i.e., removed from the lens blocking piece) for inspection.

Figure 4A:
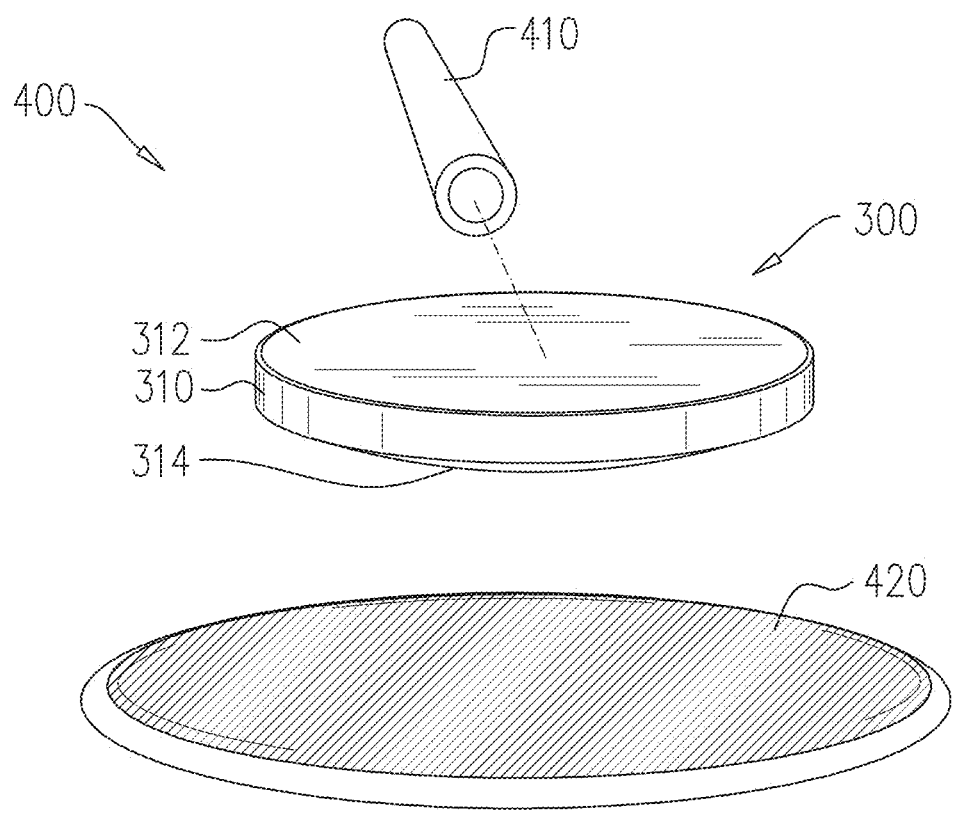
FIG. 4A is a diagram that illustrates conventional visual cosmetic inspection of a deblocked lens after machining. In a darkened room, the lens is positioned over dark/black surface and illuminated from above.
Figure 4B:
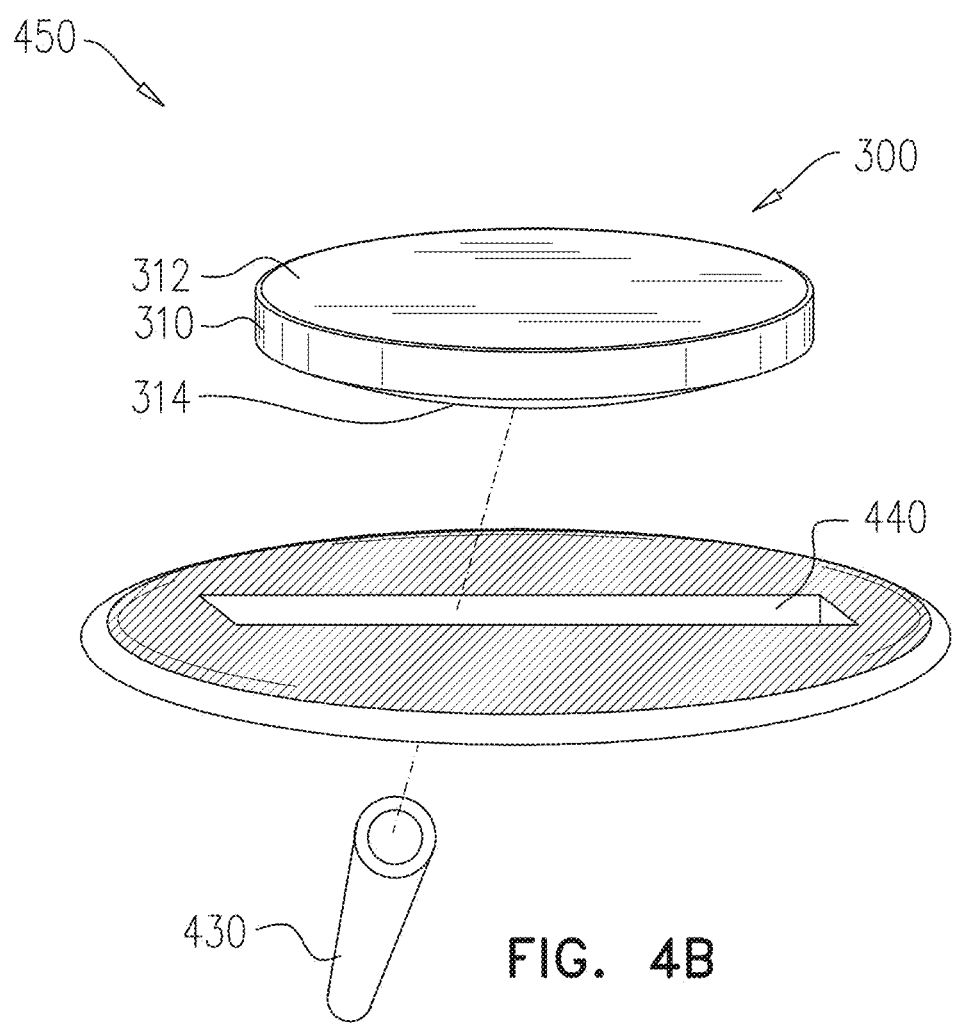
FIG. 4B is a diagram that illustrates conventional manual inspection of a deblocked lens after machining. In a darkened room, the lens is illuminated from below, and observed from above over a dark surface.

FIGS. 4A and 4B illustrate conventional configurations 400, 450 for cosmetic visual inspection of a deblocked lens 300 after backside surfacing. In the configuration 400 shown in FIG. 4A, the lens is positioned over a dark/black surface 420 and illuminated from above with a light source 410 in a darkened room. The reflections are dispersive and highlight lens defects on the front 314 and back 312 surfaces of the deblocked lens 300. In FIG. 4B, the lens 300 is illuminated with a light source 430 through a slit 440 from below a dark surface 420 and inspected from above. In this configuration 450, the transmitted light reflects dispersively and may highlight additional defects.

After inspection, the lens blank is typically blocked again in order to implement subsequent steps (e.g., coating) in lens manufacturing. Deblocking and reblocking can be time consuming and disrupt the otherwise streamlined OBM process. Moreover, if a rework is involved, the lens may undergo additional deblocking and reblocking cycles for rework, further slowing manufacturing. In most cases, however, the lack of on-block inspection methods implies that there is no in-process and on-block rework procedure in current industry practices. In conventional OBM, defects aren't generally detected after deblocking, which is normally after coating steps and can be too late and/or too costly to rework.

In lens manufacturing, it can be beneficial to inspect both the front surface and the back surface of the lens blank while the lens blank is mounted on the lens block. One technique to accentuate defects on or in the blocked lens involves preventing light from passing through the front surface of the lens. This causes light reflected from minute defects on the front and back surfaces of the lens blank to be observed more easily when viewed from the back side of the lens.

Figure 5A:
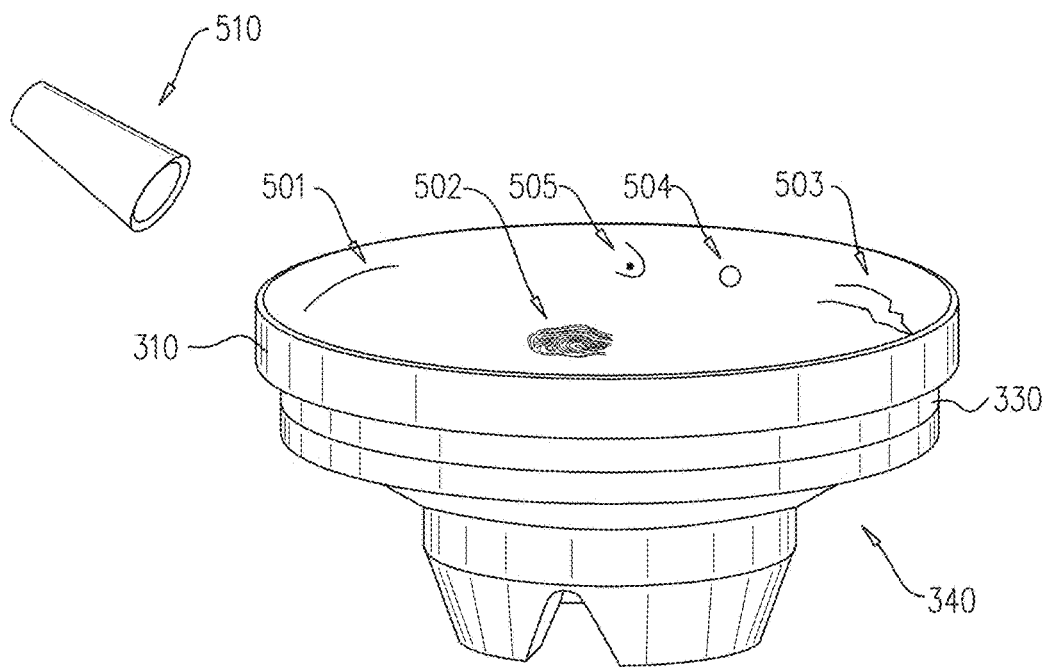
FIG. 5A is a schematic diagram of a blocked lens with different types of defects on its front and back surfaces.
Figure 5B:
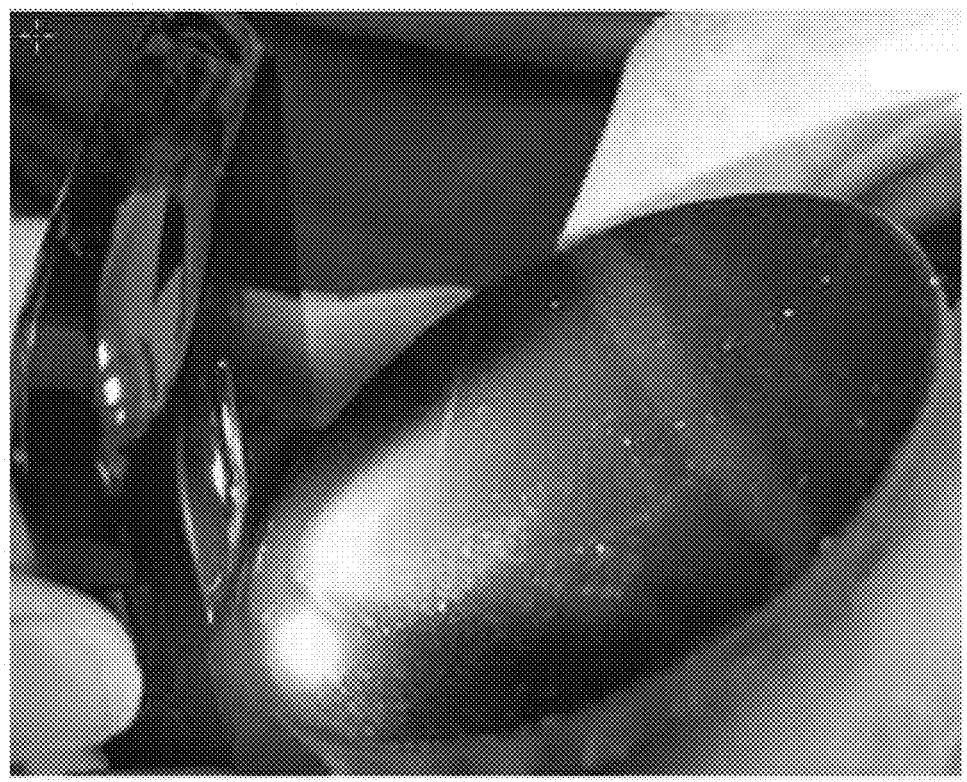
FIG. 5B is a photograph of a blocked lens with different types of defects on its front and back surfaces.

FIGS. 5A and 5B illustrate different types of defects apparent in visual inspection of a blocked lens. A light source 510 can be used to facilitate the inspection by shining light over the back surface of the lens blank 310, as shown in FIG. 5A. Possible defects that can be detected by visual inspection include a scratch 501, a contaminant 502 (e.g., a finger print), a crack 503, a dent 504, and a comet 505, among others.

There are several methods to block passage of light through the convex surface 314 of the lens, including, but not limited to:

1) Applying an opaque adhesive, such as a resin or tape, between the convex surface of the lens blank and the lens block;
2) Reducing the transparency of the materials in and/or on the lens block;
3) Coating and/or painting the convex surface of the lens blank with non-transparent materials;
4) Reducing the transparency of a surface defined by the lens block; and
5) Preventing light from reaching at least one of the lens block, the mounted front surface of the lens, or the edges of the mounted lens, e.g., using an opaque liquid or mold.

In one example, the opaque (e.g., black) adhesive described above is used to couple the lens blank and the lens blocking piece, while at the same time blocking light passage through the front surface of the lens. The black adhesive can be generated by introducing an agent (e.g., pigment) into a base adhesive that is normally used to block the lens. The agent can cause the color of the adhesive to be black in the visible region and at the same time, transparent to UV light, which is used to cure the adhesive.

More specifically, the UV curable black adhesive for OBM can comprise acrylic and epoxy-based adhesives, such as Nucleo adhesive UV 307A Eimer (Satisloh GmbH). Carbon black (pigments) can be used to introduce the black color into the base glue (resin). The incorporation of the pigments within the resins can be carried out by high shear mixing (UltraTurraxe). The pigments are added to the resin at any of several different concentration ranges from 0.1 wt % to 20 wt %. The pigments can also be dispersed and exfoliated in the resin through high shear mixing. Fine exfoliation of the pigment allows for the formation of a uniform black color of the resin, thus facilitating inspection of the lens for defects on the OBM. The pigment exfoliation procedure can be carried out at a constant temperature (e.g., 25° C.). The content of the pigment within the resin can be optimized in term of black performance and color.

The black adhesive can be characterized by parallel plate rheometer. The viscosity is measured during UV curing process. The viscosity of the resin before curing ranges from 100 to 10000 CP. After the curing process the viscosity range is 100,000 to 10 million CP.

The resulting black adhesive layer can provide low reflectance at a wavelength range of about 300 nm to about 800 nm. The reflectance can be from about 0.1% to about 5%, allowing on-block inspection.

Figure 6A:
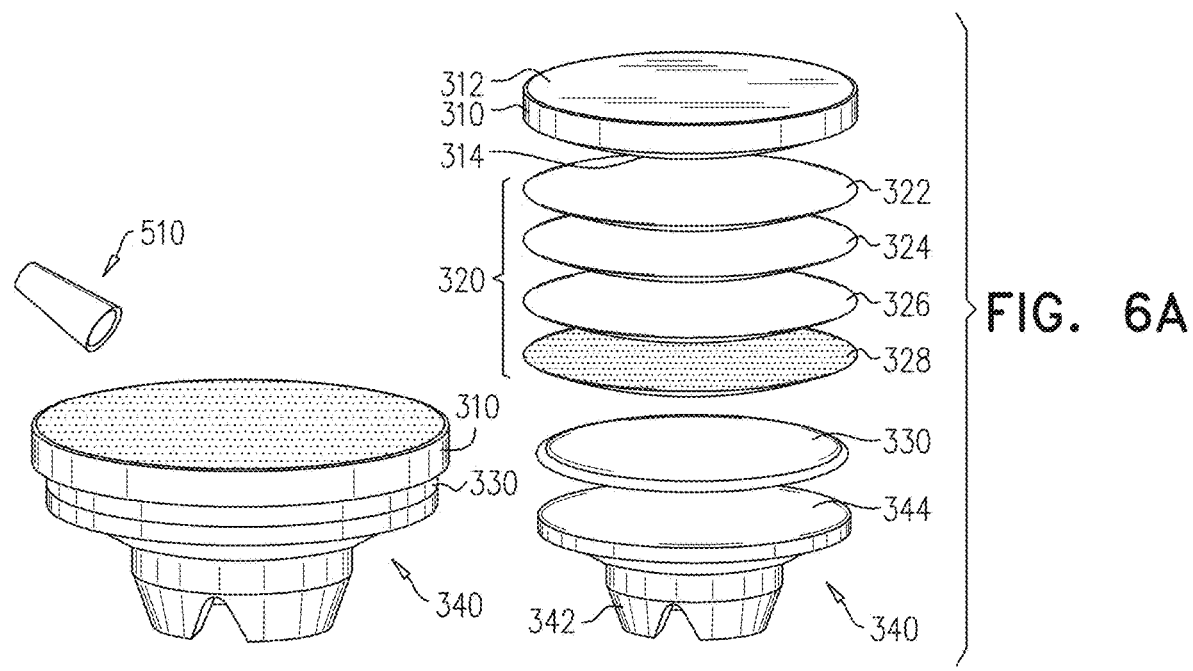
FIG. 6A is a schematic diagram of a blocked lens with a black sealing between the lens blank and the lens blocking piece.
Figure 6B:
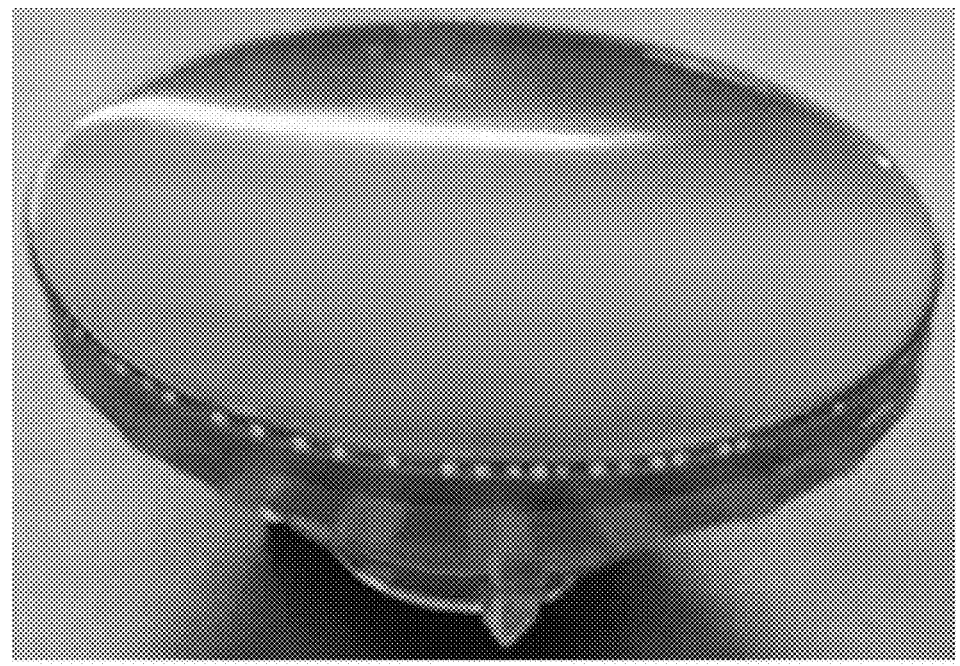
FIG. 6B is a photograph of a blocked lens with a black sealing between the lens blank and the lens blocking piece.

FIG. 6 shows another example of a blocked lens suitable for on-block inspection. In this case, on-block inspection is facilitated by a layer that reduces or prevents light from passing through the front surface of the lens. The layer can be a sealing material, paint, or film applied over the coatings layer on the front surface, or over the "grip layer" 328 or over the complete front side. In some examples, the layer can be applied on the lens edges as well. The layer can be water-based and inorganic.

Figure 7A:
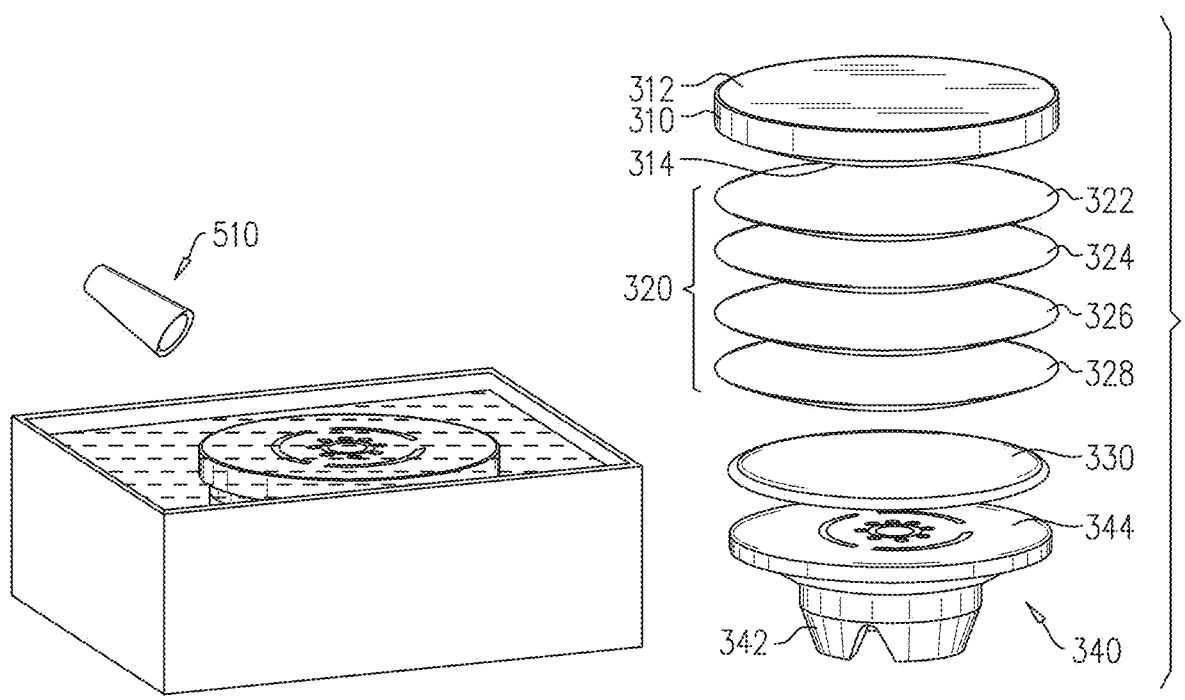
FIG. 7A is a schematic diagram of a blocked lens partially submerged in a color dye solution.
Figure 7B:
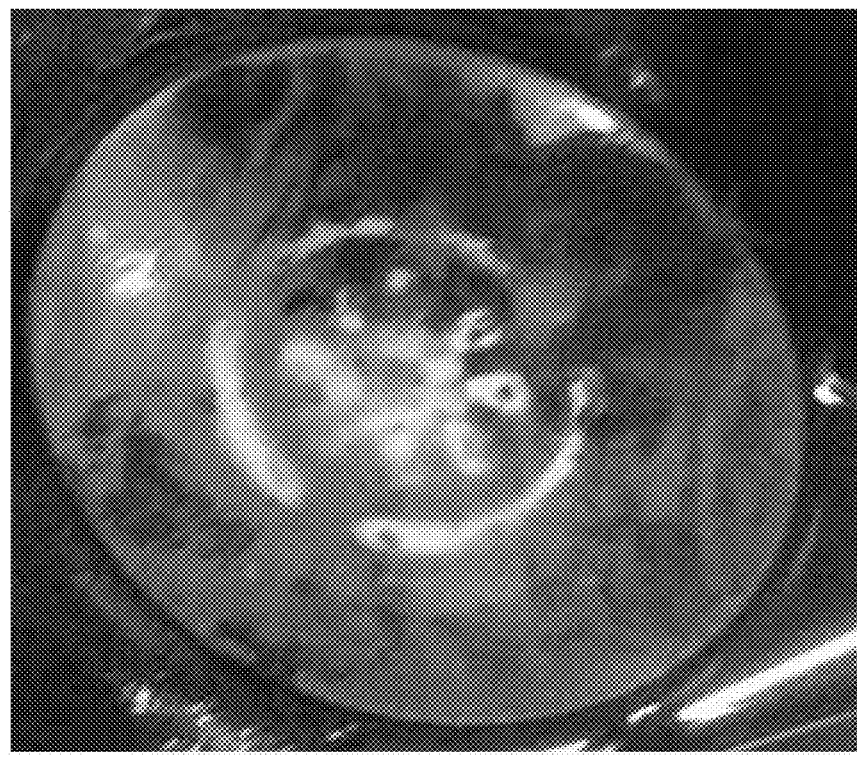
FIG. 7B is a photograph of a blocked lens partially submerged in a color dye solution.

In yet another example, as shown in FIG. 7, on-block inspection can be performed by reducing the surface transparency (e.g., in addition or instead of the body transparency) of the lens block. More specifically, the LOB can be submerged into a dark liquid containing a dye material, which can tint at least the back surface of the lens block, thereby blocking light passage through the LOB. To avoid possible contamination of the concave surface, the LOB can be submerged up to the rim of the lens blank such that the concave surface remains dry as shown in FIG. 7.

Figure 8A:
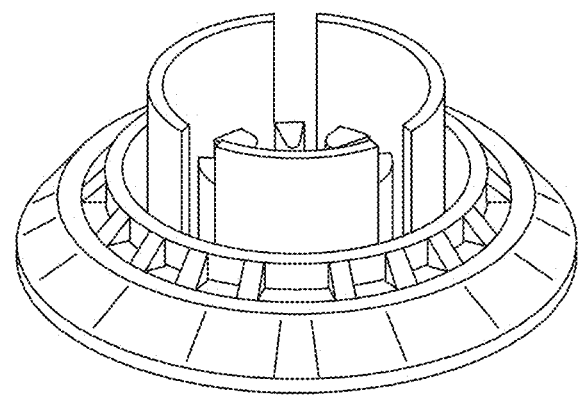
FIG. 8A is a schematic diagram of a lens blocking piece.
Figure 8B:
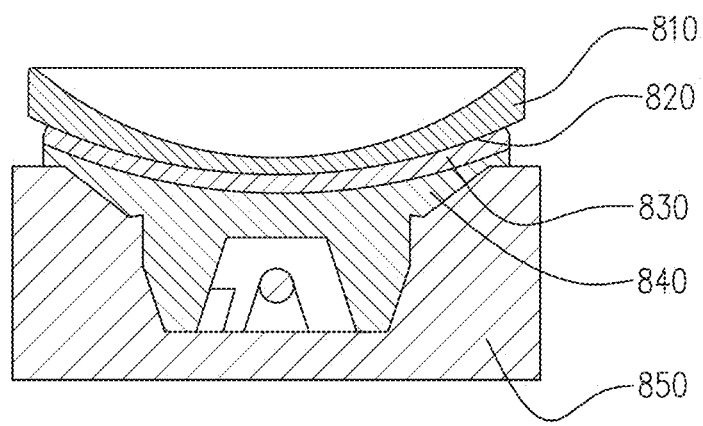
FIG. 8B is a cross-section of the profile of the blocked lens with the support structure.
Figure 8C:
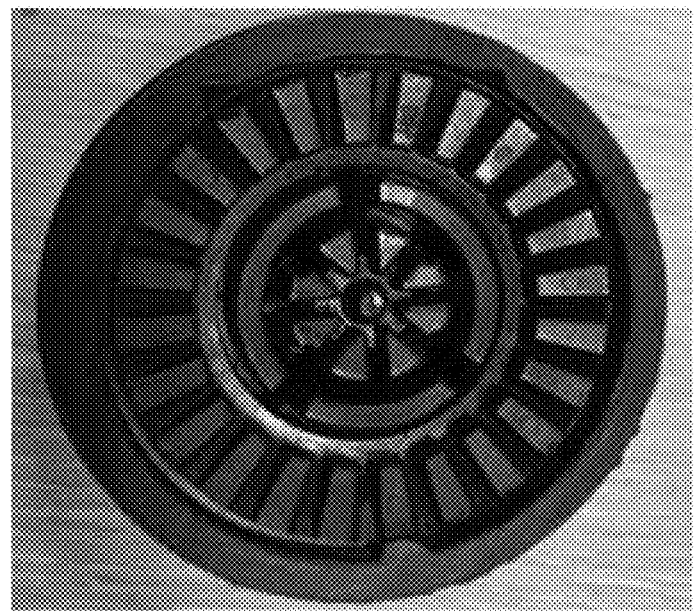
FIG. 8C is a photograph of an opaque support structure cast in the form of a "negative" of the rear surface of a lens blocking piece.

FIGS. 8A-8C show another method to make possible on-block inspection. In this method, a mold, support structure, or a fixture, which can be designed as the "negative", the "complementary", or "reverse tone" of the lens block, can be used to receive the lens block. The mold can have a non-transparent surface, or can be made from a non-transparent material such as black silicon. FIG. 8A shows the mold with a black color. When combined with the LOB into an assembly, as shown in FIG. 8B, the mold 150 can block light transmission through the assembly and therefore allow inspectors to better detect defects on the back and front surfaces by light scattered from defects on these surfaces. FIG. 8C is a photograph of an example mold of a lens blocking piece.

Figure 9A:
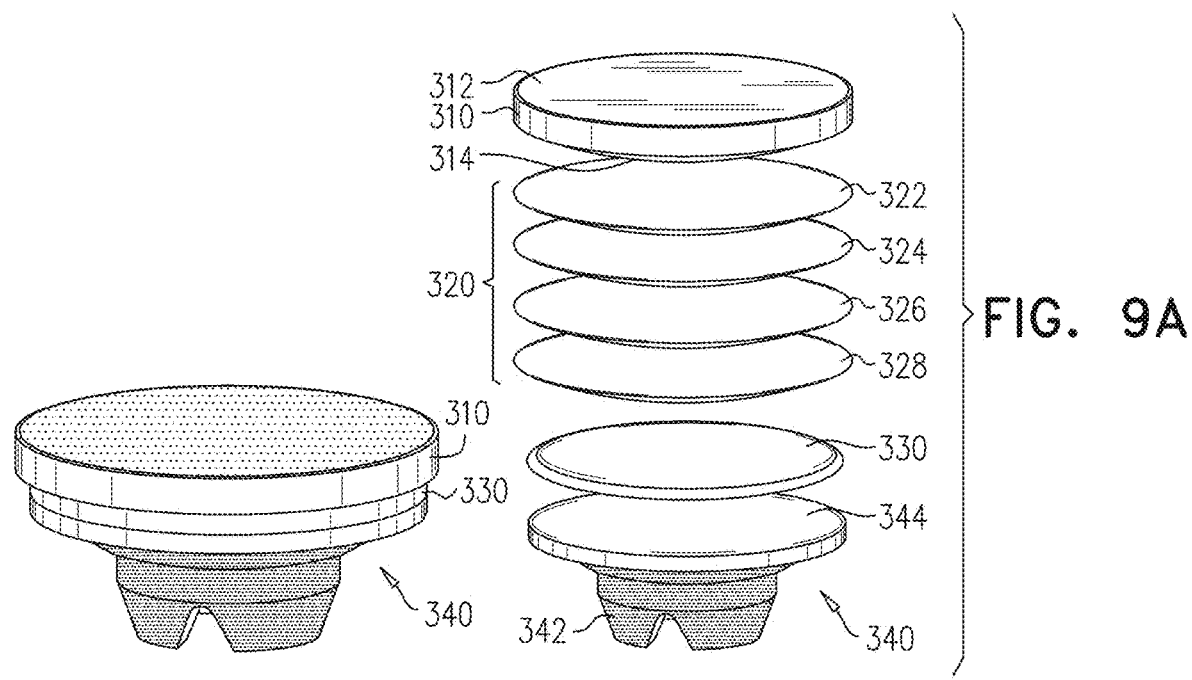
FIG. 9A is a schematic diagram of an opaque coating (painting) disposed on the rear surface of a transparent lens blocking piece.
Figure 9B:
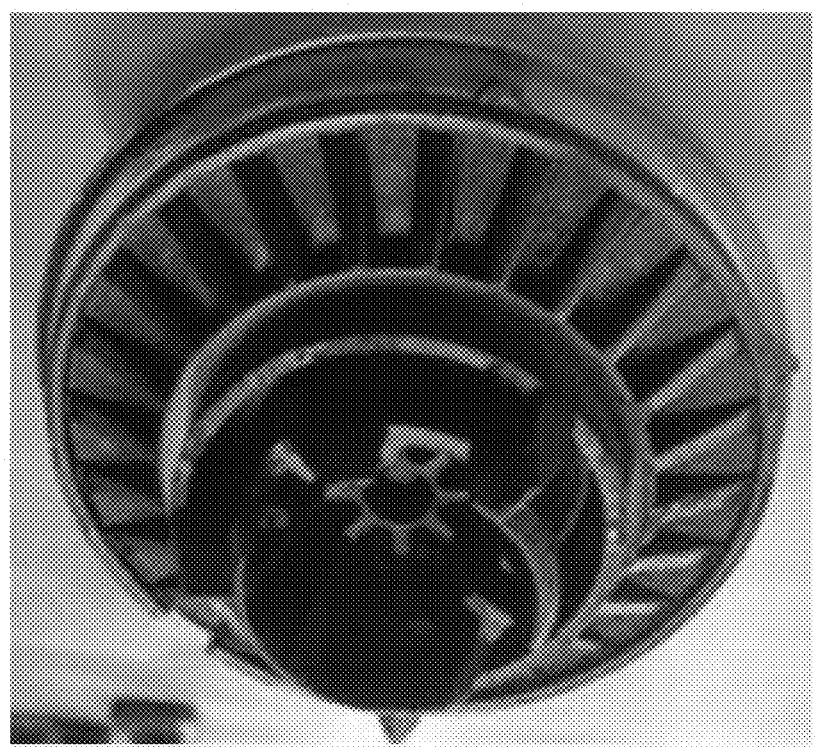
FIG. 9B is a photograph of an opaque coating (painting) disposed on the rear surface of a transparent lens blocking piece.

FIG. 9 shows a lens block that is painted on the back surface to prevent visible light from passing through the lens block. Alternatively, a soft, removable coating can be applied to the block surface, such that the coating can be peeled away if needed.

Once light transmission through the LOB is obstructed, several lighting arrangements can be designed to increase the visibility of minute defects on or close to the lens surfaces, facilitating on-block inspection.

Figure 10:
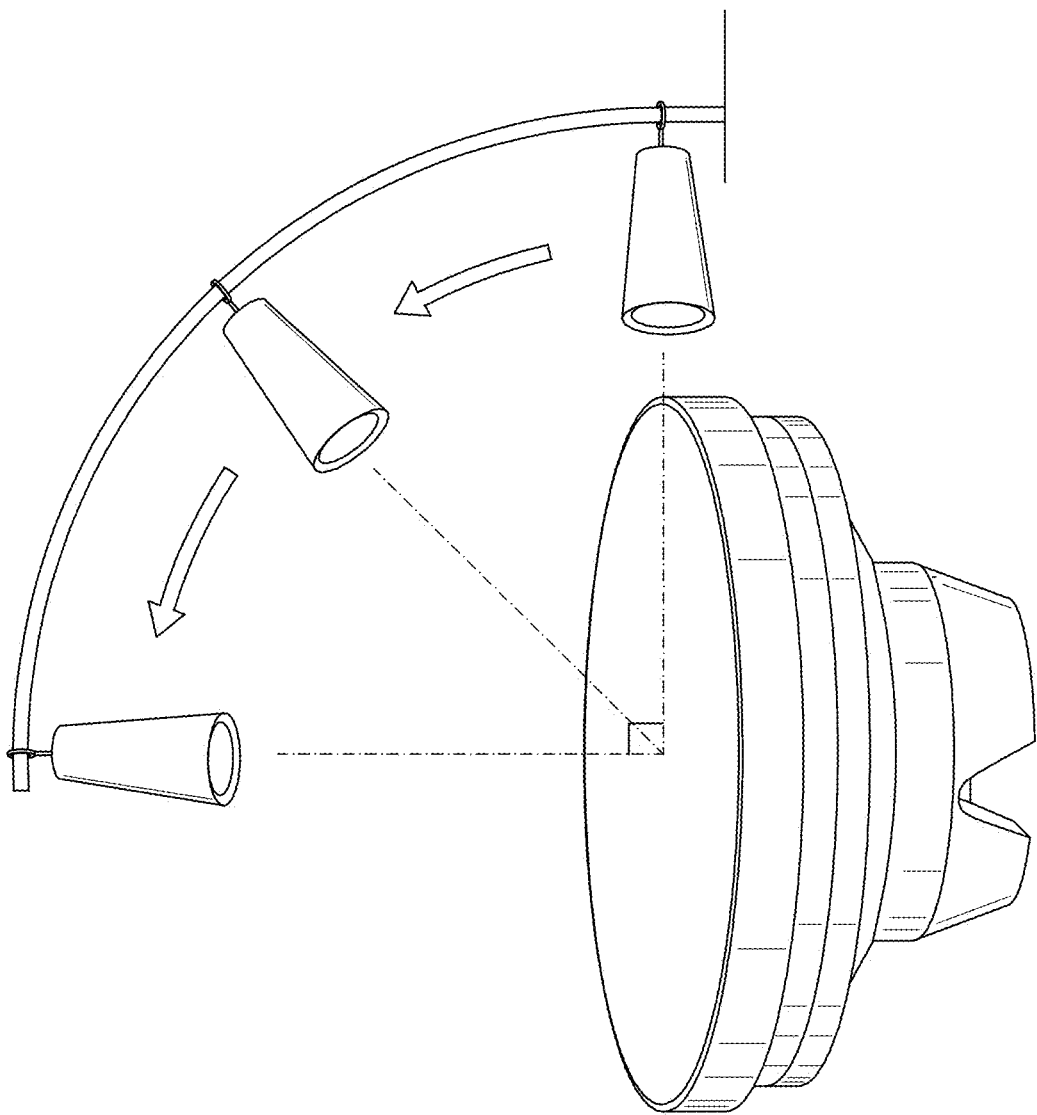
FIG. 10 is a diagram illustrating illumination of the concave surface of a blocked lens with illumination within a plane comprising the optical axis of the lens blank.

In one example, as shown in FIG. 10, the light source can be disposed at different locations within a plane perpendicular to the concave surface (i.e., in a plane comprising the optical axis of the lens blank). These different locations result in different incidence angles, which can range from normal incident to nearly grazing incidence, allowing an inspector to observe light scattered by possible defects from a wide range of angles.

Figure 11:
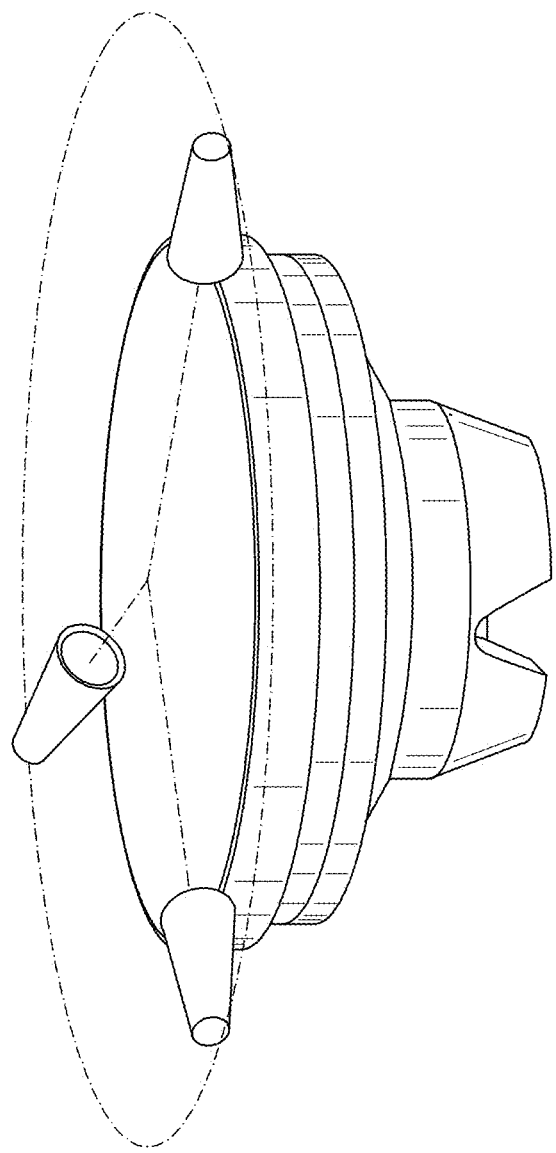
FIG. 11 is a diagram illustrating illumination of the concave surface of a blocked lens with illumination within a plane normal to the optical axis of the lens blank.

In another example, as shown in FIG. 11, the light source can be applied at different angles with respect to the concave surface. One or more light sources can be arranged along a locus of points in a plane perpendicular to the optical axis of the lens blank (e.g., a circle or an arc centered about the optical axis).

Figure 12:
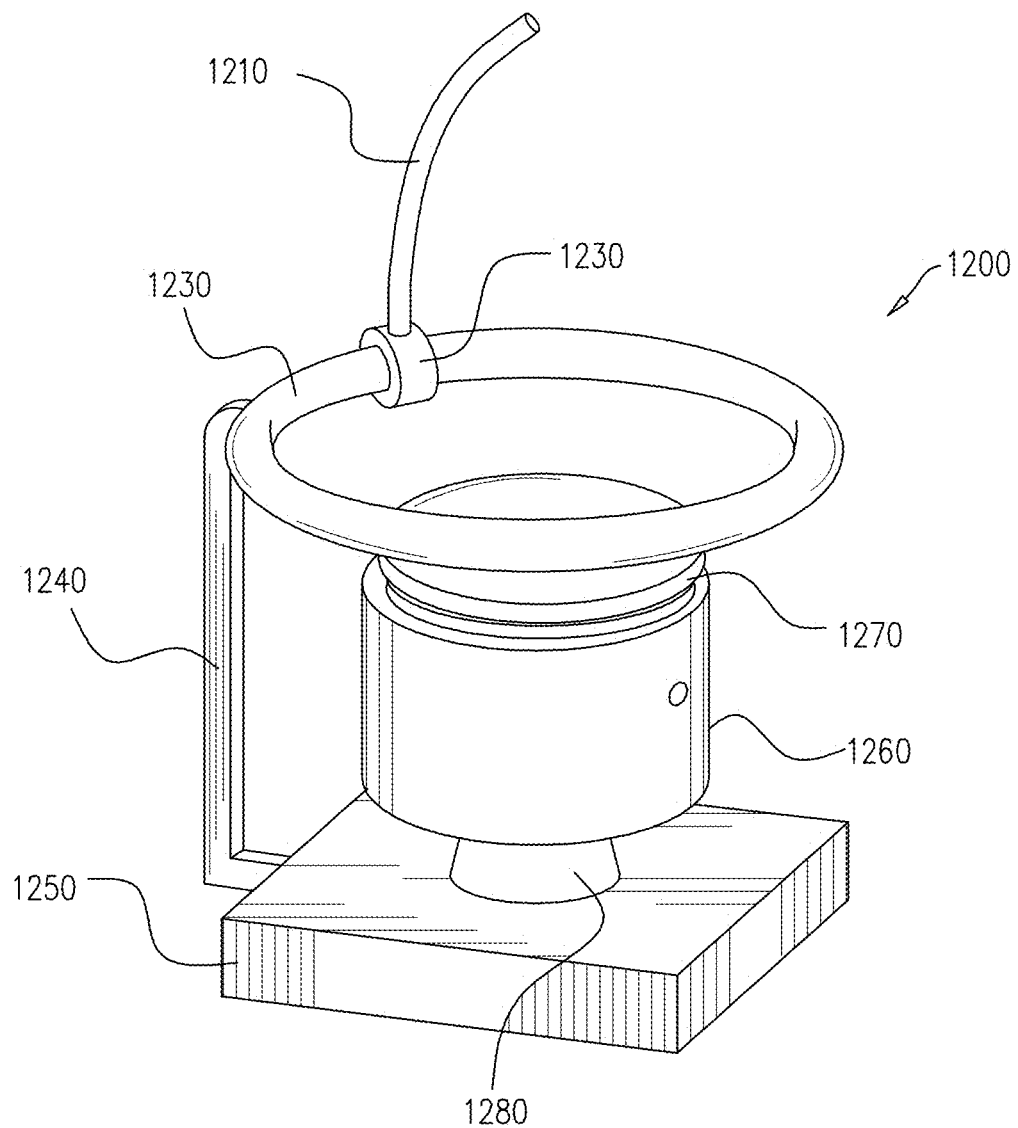
FIG. 12 is a perspective view of a ring light for inspection of a blocked lens.

Alternatively, a ring light source, as showed in FIG. 12, can be used to illuminate the blocked lens. In the system 1200 shown in FIG. 12, a ring light source 1230 is disposed above a blocked lens 1270 via a supporting structure 1240. The blocked lens 1270 is placed in a holder 1260 which can hold the blocked lens 1270 by, for example, receiving the back of the blocking piece in the blocked lens. The system 1200 also includes a base 1250 connecting to the supporting structure 1240 so as to support the ring light source 1230. The base 1250 also receives and supports the holder 1260 via a pivoting member 1280. In operation, the pivoting member 1280 allows an inspector to tilt and rotate the blocked lens 1270 so as to identify possible defects. The distance between the light source and the concave surface can be adjusted to achieve the desired illumination of the concave surface and any defects upon it.

In yet another example, an additional vertical light 1210 can be disposed on top of the ring light 1230 to achieve enhanced illumination, as shown in FIG. 12. The two light sources may deliver different wavelengths (colors) such that one wavelength can be used as a background for the other to increase a contrast of the image of defects. Furthermore, different types of defects may scatter different wavelengths. By using two or more wavelengths for the light sources, the chance of detecting defects can be accordingly increased. Alternatively, the two light sources may also deliver lights of different polarizations to illuminate defects of different orientations.

Figure 13A:
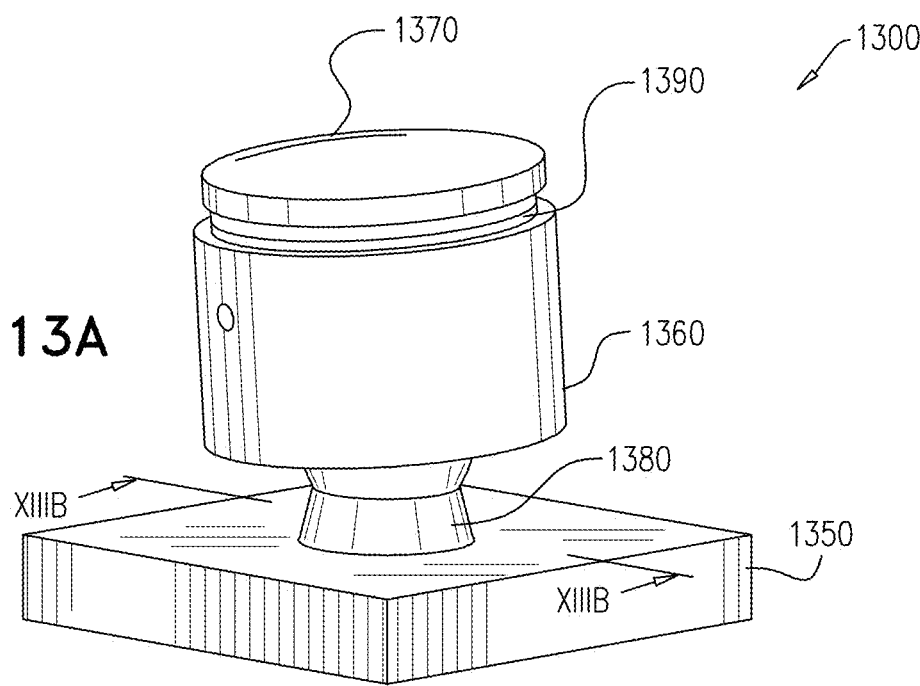
FIG. 13A is a perspective view of a stand for inspection of a blocked lens.
Figure 13B:
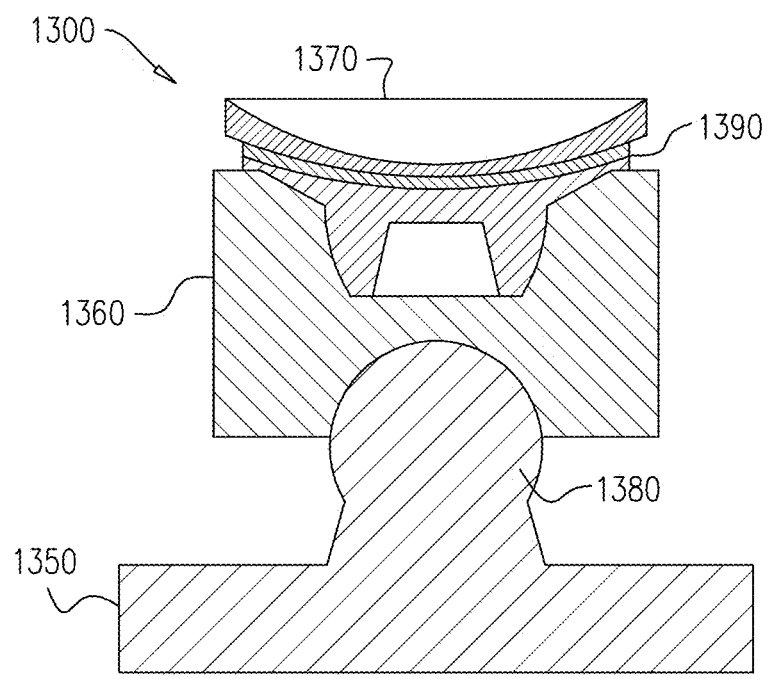
FIG. 13B is a cross-section of a profile of the stand shown in FIG. 13A.

An on-block inspection holding system, as shown in FIGS. 13A and 13B, can be used to mount the LOB. FIG. 13A shows a perspective view of a holding system 1300, which includes a base 1350 supporting a holder 1360 via a pivoting member 1380. The holder 1360 can receive a blocked lens 1370 by coupling to the back of the lens blocking piece in the blocked lens 1370. The blocked lens 1370 can include an opaque layer 1390 so as to facilitate on-block inspection. The opaque layer 1390 can be, for example, an opaque adhesive, an opaque coating, or an opaque painting, as discussed before. FIG. 13B shows a cross sectional view of the lens holding system 1300. The holder can allow tilting and rotation of the LOB to direct the incident and reflect light in different directions for inspection.

On-Block Optical Property Measurements

In conventional ophthalmic lens manufacturing processes, the front surface of the blocked lens may have residual strains that are relieved after de-blocking. These strains affect the lens's optical properties and complicate measurement of certain optical properties while the lens is blocked. As a result, these optical properties are measured accurately after de-blocking.

A focimeter or lensmeter is normally used in traditional measurements of optical properties. Rays of light are transmitted through the measuring location on or in the lens, and deviation of the rays as a result of passing through the lens is recorded and translated into optical power(s). The measured optical powers can depend on several factors, including the local geometry of the back/front surface at the location of light incidence, the refractive index of the material, and the lens thickness.

In one exemplary embodiment, an opaque material, disposed between the front surface of the lens blank and the lens blocking piece, can allow on-block measurement of optical measurement. The optical measurement can be done by reflection methods, in which rays of light are reflected from the back surface, and the angle of reflection is measured and translated to local geometry (surface curvature). Using the known index of refraction of the material, the measured geometry can be further converted to surface optics. In order to receive accurate optical representation of the back surface, elimination of unwanted reflection (e.g., from other surfaces other than the back surface) can be helpful.

CONCLUSION

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, embodiments of designing and making the coupling structures and diffractive optical elements disclosed herein may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities, including a Personal Digital Assistant (PDA), a smart phone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

The various methods or processes (e.g., of designing and making the coupling structures and diffractive optical elements disclosed above) outlined herein may be coded as software that is executable on one or more processors that employ any one of a variety of operating systems or platforms. Additionally, such software may be written using any of a number of suitable programming languages and/or programming or scripting tools, and also may be compiled as executable machine language code or intermediate code that is executed on a framework or virtual machine.

In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computer or other processor to implement various aspects of embodiments as discussed above. Additionally, it should be appreciated that according to one aspect, one or more computer programs that when executed perform methods of the present invention need not reside on a single computer or processor, but may be distributed in a modular fashion amongst a number of different computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A blocked lens for on-block processing and visual inspection, the blocked lens comprising:
    a lens blank having a front surface and a back surface;
    a lens blocking piece, affixed to the front surface of the lens blank, to hold the lens blank while processing the back surface of the lens blank; and
    an opaque material, in optical communication with the back surface of the lens blank and the front surface of the lens blank, to absorb visible light propagating through the back surface of the lens blank towards the front surface of the lens blank so as to facilitate inspection of the back surface of the lens blank while the lens blocking piece is affixed to the front surface of the lens blank, wherein the opaque material comprises an opaque layer of adhesive disposed between the front surface of the lens blank and the lens blocking piece.

2. The blocked lens of claim 1, wherein the opaque layer of adhesive comprises:
    a resin, disposed between the front surface of the lens blank and the lens blocking piece, to affix the lens blank to the lens blocking piece; and
    a pigment, dispersed within the resin, to absorb at least a portion of the visible light propagating through the back surface of the lens blank.

3. The blocked lens of claim 2, wherein the pigment comprises at least one of carbon black, charcoal, aniline, or chromophoric-based dye.

4. The blocked lens of claim 1, wherein the opaque material is configured to affix the lens blank to the lens blocking piece and to absorb at least a portion of the visible light transmitted through the back surface of the lens blank towards the front surface of the lens blank.

5. The blocked lens of claim 1, wherein the opaque material comprises an opaque coating disposed on a surface of the lens blocking piece.

6. A method of inspecting a blocked lens, the blocked lens including:
    a lens blank having a front surface and a back surface;
    a lens blocking piece affixed to the front surface of the lens blank; and
    an opaque material in optical communication with the back surface of the lens blank and the front surface of the lens blank, the opaque material comprising an opaque layer of adhesive disposed between the front surface of the lens blank and the lens blocking piece,
    the method comprising, while the lens blocking piece is affixed to the front surface of the lens blank:

(A) illuminating the opaque material, via the back surface of the lens blank, with visible light so as to render at least one defect on or proximate to the lens blank apparent to a human eye; and (B) inspecting the lens blank for defects.

7. The method of claim 6, wherein (A) comprises illuminating the back surface of the lens blank at a plurality of angles of incidence in a plane comprising an optical axis of the lens blank.

8. The method of claim 6, wherein (A) comprises illuminating the back surface of the lens blank at a plurality of angles of incidence in a plane normal to an optical axis of the lens blank.

9. The method of claim 6, wherein (B) comprises inspecting the back surface of the lens blank for defects.

10. The method of claim 6, wherein (B) comprises inspecting a body of the lens blank for defects.

11. The method of claim 6, wherein (B) comprise inspecting the front surface of the lens blank for defects.

12. A method of processing a blocked lens comprising a lens blank affixed to a lens blocking piece, the lens blank defining a back surface, the method comprising:
   A) processing the back surface of the lens blank according to a predetermined prescription while the lens blank is affixed to the lens blocking piece;
   B) inspecting the back surface of the lens blank while the lens blank is affixed to the lens blocking piece; and
   C) in response to detection of at least one defect correctable by processing the back surface of the lens blank, processing the back surface of the lens blank while the lens blank is affixed to the lens blocking piece,
   wherein an opaque material comprising an opaque layer of adhesive is disposed between a front surface of the lens blank and the lens blocking piece.

13. The method of claim 12, wherein A) comprises at least one of machining, polishing, coating, tinting, or cleaning the back surface of the lens blank.

14. The method of claim 12, wherein C) comprises removing material from at least a portion of the back surface of the lens blank.

15. The method of claim 12, wherein C) comprises cleaning the blocked lens.

16. The method of claim 12, further comprising:
D) inspecting the back surface of the lens blank while the lens blank is affixed to the lens blocking piece after processing the back surface of the lens blank in C).

17. The method of claim 16, further comprising:
E) in response to inspection of the back surface of the lens blank in D), processing the back surface of the lens blank while the lens blank is affixed to the lens blocking piece.

18. The method of claim 12, wherein C) comprises:
removing at least a portion of a first coating from the back surface while the lens blank is affixed to the lens blocking piece;
altering a shape of the back surface of the lens blank while the lens blank is affixed to the lens blocking piece; and
depositing a second coating on the back surface of the lens blank.

19. The method of claim 12, wherein A) comprises:
machining a back surface of the blocked lens to provide an optical power prescribed for the patient;
polishing the back surface of the blocked lens;
cleaning the back surface of the blocked lens;
wherein B) comprises:
identifying the at least one defect near the back surface of the blocked lens;
wherein C) comprises:
processing the back surface of the blocked lens based at least in part on the at least one defect; and further comprising:
depositing at least one of a hard coating layer or an anti-reflection coating on the back surface of the blocked lens;
removing the lens blank from the lens blocking piece;
marking an orientation of the lens blank for framing an ophthalmic lens in a lens frame; and
edging the lens blank to form the ophthalmic lens.

20. The method of claim 12, wherein C) comprises:
illuminating the opaque material via a back surface of the blocked lens so as to scatter or reflect light from the back surface of the blocked lens.

* * * * *